United States Patent
Pizcueta Lalanza et al.

(10) Patent No.: US 11,938,122 B2
(45) Date of Patent: Mar. 26, 2024

(54) 5-[[4-[2-[5-(1-HYDROXYETHYL)PYRIDIN-2-YL]ETHOXY]PHENYL]METHYL]-1,3-THIAZOLIDINE-2,4-DIONE FOR TREATING NONALCOHOLIC FATTY LIVER DISEASE

(71) Applicant: Minoryx Therapeutics S.L., Mataró Barcelona (ES)

(72) Inventors: Maria Pilar Pizcueta Lalanza, Barcelona (ES); Marc Martinell Pedemonte, Barcelona (ES)

(73) Assignee: Minoryx Therapeutics S.L., Barcelona (ES)

( * ) Notice: Subject to any disclaimer, the term of this patent is extended or adjusted under 35 U.S.C. 154(b) by 0 days.

(21) Appl. No.: 16/465,043

(22) PCT Filed: Dec. 1, 2017

(86) PCT No.: PCT/IB2017/057587
§ 371 (c)(1),
(2) Date: May 29, 2019

(87) PCT Pub. No.: WO2018/100557
PCT Pub. Date: Jun. 7, 2018

(65) Prior Publication Data
US 2020/0093812 A1  Mar. 26, 2020

(30) Foreign Application Priority Data
Dec. 1, 2016  (EP) ..................................... 16382584

(51) Int. Cl.
*A61K 31/4439* (2006.01)
*A61K 9/08* (2006.01)
(Continued)

(52) U.S. Cl.
CPC ............ *A61K 31/4439* (2013.01); *A61K 9/08* (2013.01); *A61K 9/16* (2013.01); *A61K 9/20* (2013.01); *A61K 9/48* (2013.01); *A61P 1/16* (2018.01)

(58) Field of Classification Search
CPC ...... A61K 31/4439; A61K 45/06; A61K 9/08; A61K 9/16; A61K 9/20; A61K 9/48; A61P 1/16
(Continued)

(56) References Cited

U.S. PATENT DOCUMENTS 5,441,971 A   8/1995  Sohda et al.
6,100,403 A   8/2000  Saito et al.
(Continued)

FOREIGN PATENT DOCUMENTS

EP   1 465 627 B1   3/2006
EP   1 133 294 B1   8/2010
(Continued)

OTHER PUBLICATIONS

Clark, Jeanne Mary (The epidemiology of nonalcoholic fatty liver disease in adults. J Clin Gastroenterol. Mar. 2006;40 Suppl 1:S5-10. doi: 10.1097/01.mcg.0000168638.84840.ff.( Abstract )PMID: 16540768).*

(Continued)

*Primary Examiner* — Bethany P Barham
*Assistant Examiner* — Barbara S Frazier
(74) *Attorney, Agent, or Firm* — Sterne, Kessler, Goldstein & Fox P.L.L.C.

(57) ABSTRACT

The present disclosure relates to a method of treating or preventing nonalcoholic fatty liver disease, nonalcoholic steatohepatitis, a chronic granulomatous disorder, a polycystic ovary syndrome, a thyroid carcinoma, a thyroid autoimmune disorder, a pituitary adenoma, atherosclerosis, hyper- (Continued)

tension, a skin disease, an inflammation and autoimmune disease, and an inflammatory respiratory disease by administering 5-[[4-[2-[5-(1-hydroxyethyl)pyridin-2-yl]ethoxy]phenyl]methyl]-1,3-thiazolidine-2,4-dione to a subject in need thereof. The disclosure also relates to 5-[[4-[2-[5-(1-hydroxyethyl)pyridin-2-yl]ethoxy]phenyl]methyl]-1,3-thiazolidine-2,4-dione for use in a pharmaceutical composition or in the manufacture of a medicament for the treatment or prevention of nonalcoholic fatty liver disease or nonalcoholic steatohepatitis.

13 Claims, 8 Drawing Sheets

(51) Int. Cl.
    *A61K 9/16* (2006.01)
    *A61K 9/20* (2006.01)
    *A61K 9/48* (2006.01)
    *A61P 1/16* (2006.01)

(58) Field of Classification Search
    USPC ........................................................ 514/342
    See application file for complete search history.

(56) References Cited

U.S. PATENT DOCUMENTS

| | | |
|---|---|---|
| 6,191,154 B1 | 2/2001 | Landreth et al. |
| 6,294,192 B1 | 9/2001 | Patel et al. |
| 6,451,339 B2 | 9/2002 | Patel et al. |
| 6,720,001 B2 | 4/2004 | Chen et al. |
| 8,389,556 B2 | 3/2013 | Colca et al. |
| 8,722,710 B2 | 5/2014 | Czarnik |
| 8,865,747 B2 | 10/2014 | Pujol Onofre |
| 8,895,536 B2 | 11/2014 | Bannister et al. |
| 8,895,537 B2 | 11/2014 | Bannister et al. |
| 8,969,581 B2 | 3/2015 | Witt |
| 9,782,395 B2 * | 10/2017 | García Collazo ....... A61P 29/00 |
| 10,179,126 B2 * | 1/2019 | García Collazo ....... A61P 35/00 |
| 2013/0274295 A1 | 10/2013 | Pujol Onofre |
| 2014/0088127 A1 | 3/2014 | Pandey et al. |
| 2014/0178456 A1 | 6/2014 | Devanaboyina |
| 2014/0243377 A1 | 8/2014 | Czarnik |
| 2014/0275180 A1 | 9/2014 | DeWitt |
| 2015/0224120 A1 | 8/2015 | Clelland et al. |
| 2015/0284346 A1 | 10/2015 | DeWitt |
| 2019/0255032 A1 | 8/2019 | García Collazo |

FOREIGN PATENT DOCUMENTS

| | | |
|---|---|---|
| WO | WO 92/18501 A1 | 10/1992 |
| WO | WO 93/22445 A1 | 11/1993 |
| WO | WO-2006125285 A1 | 11/2006 |
| WO | WO 2013/040419 A1 | 3/2013 |
| WO | WO 2014/152843 A1 | 9/2014 |
| WO | WO 2015/109037 A1 | 7/2015 |
| WO | WO-2015150476 A1 | 10/2015 |
| WO | WO-2018100557 A1 | 6/2018 |

OTHER PUBLICATIONS

Kawaguchi-Suzuki M, (J Chromatogr B Analyt Technol Biomed Life Sci. Oct. 15, 2014;969:219-23. doi: 10.1016/j.jchromb.2014.08.019. Epub Aug. 21, 2014. PMID: 25195022.).*

Yau Hanford, (The future of thiazolidinedione therapy in the management of type 2 diabetes mellitus. Curr Diab Rep. Jun. 2013;13(3):329-41. doi: 10.1007/s11892-013-0378-8. PMID: 23625197).*

Alkhouri, N., et al., "Neutrophil to Lymphocyte Ratio: A New Marker for Predicting Steatohepatitis and Fibrosis in Patients With Nonalcoholic Fatty Liver Disease," Liver International 32(2):297-302, Wiley-Blackwell, United States (2012).

Belfort, R., et al., "A Placebo-Controlled Trial of Pioglitazone in Subjects with Nonalcoholic Steatohepatitis," The New England Journal of Medicine 355(22):2297-2307, Massachusetts Medical Society, United States (2006).

Belvisi, M.G., et al., "Peroxisome Proliferator-Activated Receptor Gamma Agonists as Therapy for Chronic Airway Inflammation," European Journal of Pharmacology 533(1-3):101-109, Elsevier Science, Netherlands (2006).

Buechler, C., et al., "Adiponectin, a Key Adipokine in Obesity Related Liver Diseases," World Journal of Gastroenterology 17(23):2801-2811, Baishideng Publishing Group, United States (2011).

Christensen, M.L., et al., "Single- and Multiple-Dose Pharmacokinetics of Pioglitazone in Adolescents with Type 2 Diabetes," The Journal of Clinical Pharmacology 45(10):1137-1144, John Wiley & Sons, England (2005).

Du, Q., et al., "Effects of Thiazolidinediones on Polycystic Ovary Syndrome: A Meta-Analysis of Randomized Placebo-Controlled Trials," Advances in Therapy 29(9):763-774, Health Communications Inc, United States (2012).

Eckland, D.A., and Danhof, M., "Clinical Pharmacokinetics of Pioglitazone," Experimental and Clinical Endocrinology & Diabetes 108(Supp 2): S234-S242, Thieme, United States (2000).

Ellis, C.N., et al., "Troglitazone Improves Psoriasis and Normalizes Models of Proliferative Skin Disease: Ligands for Peroxisome Proliferator-Activated Receptor-Gamma Inhibit Keratinocyte Proliferation," Archives of Dermatology 136(5):609-616, American Medical Association, United States (2000).

Farrell., G., et al., "Overview: an introduction to NASH and related fatty liver disorders," in Fatty Liver Disease: NASH and Related Fatty Liver Disorders, pp. 1-12, John Wiley & Sons, United States (2007).

Ferrari, S.M., et al., "Peroxisome Proliferator-Activated Receptor-γ in Thyroid Autoimmunity," PPAR Research 2015(ID 232818):1-9, Hindawi, England (2015).

Grommes, C., et al., "Antineoplastic Effects of Peroxisome Proliferator-Activated Receptor Gamma Agonists," The Lancet Oncology 5(7):419-429, The Lancet Publishing Group, England (2004).

Heaney, A.P., et al., "PPAR-Gamma Receptor Ligands: Novel Therapy for Pituitary Adenomas," Journal of Clinical Investigation 111(9):1381-1388, American Society for Clinical Investigation, United States (2003).

Hsueh, W.A., and Law, R.E., "PPARgamma and Atherosclerosis: Effects on Cell Growth and Movement," Arteriosclerosis, Thrombosis, and Vascular Biology 21(12): 1891-1895, Lippincott Williams & Wilkins, United States (2001).

Imajo, K., et al., "Rodent Models of Nonalcoholic Fatty Liver Disease/Nonalcoholic Steatohepatitis," International Journal of Molecular Sciences 14(11):21833-21857, MDPI, Switzerland (2013).

International Search Report and Written Opinion for International Application No. PCT/IB2017/057587, European Patent Office, H.V Rijswijk, dated Apr. 10, 2018, 16 pages.

Kamada, Y., et al., "Enhanced Carbon Tetrachloride-Induced Liver Fibrosis in Mice Lacking Adiponectin," Gastroenterology 125(6):1796-1807, W.B. Saunders, United States (2003).

Kaser, S., et al., "Adiponectin and its Receptors in Non-Alcoholic Steatohepatitis," Gut 54(1):117-121, British Medical Association, England (2005).

Kawaguchi-Suzuki, M., et al., "A Validated Liquid Chromatography Tandem Mass Spectrometry Method for Simultaneous Determination of Pioglitazone, Hydroxypioglitazone, and Ketopioglitazone in Human Plasma and its Application to a Clinical Study," Journal of Chromatography B: Analytical Technologies in the Biomedical and Life Sciences 969:219-223, Elsevier, Netherlands ( 2014).

Kawaguchi-Suzuki, M., et al., "Concentration-Dependent Response to Pioglitazone in Nonalcoholic Steatohepatitis" Alimentary Pharmacology & Therapeutics 46(1):56-61, Wiley-Blackwell, England (Jul. 2017).

Kleiner, D.E., et al., "Design and Validation of a Histological Scoring System for Nonalcoholic Fatty Liver Disease," Hepatology 41(6): 1313-1321, John Wiley & Sons, United States (2005).

(56) References Cited

OTHER PUBLICATIONS

Kus, V., et al., "Unmasking Differential Effects of Rosiglitazone and Pioglitazone in the Combination Treatment with N-3 Fatty Acids in Mice Fed a High-Fat Diet," PLoS One 6(11):1-14, Public Library of Science, United States (2011).

Machado, M.V., et al., "Mouse Models of Diet-Induced Nonalcoholic Steatohepatitis Reproduce the Heterogeneity of the Human Disease," PLoS One 10(5):1-16, Public Library of Science, United States (2015).

Maeshiba, Y., et al., "Disposition of the New Antidiabetic Agent Pioglitazone in Rats, Dogs, and Monkeys," Arzneimittel-Forschung/ Drug Research 47(I):29-35, Editio Cantor, Germany (1997).

Martelli, M.L., et al., "Inhibitory Effects of Peroxisome Proliferator-Activated Receptor Gamma on Thyroid Carcinoma Cell Growth," The Journal of Clinical Endocrinology and Metabolism 87(10):4728-4735, Oxford University Press, United States (2002).

Migliavacca, M., et al., "Pioglitazone as a Novel Therapeutic Approach in Chronic Granulomatous Disease," The Journal of Allergy and Clinical Immunology 137(6):1913-1915, Mosby, United States (Jun. 2016).

Moss, G.P., "Basic Terminology of Stereochemistry," Pure and Applied Chemistry 68(12):2193-2222, International Union of Pure and Applied Chemistry, England (1996).

Nakamura, A., and Terauchi, Y., "Lessons from Mouse Models of High-Fat Diet-Induced NAFLD," International Journal of Molecular Sciences 14(11):21240-21257, MDPI, Switzerland (2013).

Pershadsingh, H.A., "Peroxisome Proliferator-Activated Receptor-Gamma: Therapeutic Target for Diseases Beyond Diabetes: Quo Vadis?," Expert Opinion on Investigational Drugs 13(3):215-228, Taylor & Francis, England (2004).

Sahi, J., et al., et al., "Comparative Effects of Thiazolidinediones on In Vitro P450 Enzyme Induction and Inhibition," Drug Metabolism and Disposition 31(4):439-446, American Society for Pharmacology and Experimental Therapeutics, United States ( 2003).

Sanyal, A.J., et al., "Pioglitazone, Vitamin E, or Placebo for Nonalcoholic Steatohepatitis," The New England Journal of Medicine 362(18):1675-1685, Massachusetts Medical Society, United States (2010).

Singh, U., et al., "Development of an in Vitro Screening Assay to Test the Anti-inflammatory Properties of Dietary Supplements and Pharmacologic Agents," Clinical Chemistry 51(12):2252-2256, Oxford University Press, England (2005).

Sohda, T., et al., "Studies on Antidiabetic Agents. XII. Synthesis and Activity of the Metabolites of (+/−)-5-[p-[2-(5-ethyl-2-pyridyl)ethoxy]benzyl]-2,4-thiazolidinedione (Pioglitazone)," Chemical and Pharmaceutical Bulletin 43(12):2168-2172, Pharmaceutical Society of Japan, Japan (1995).

Suzuki, S., et al., "Effects of Pioglitazone, a Peroxisome Proliferator-activated Receptor Gamma Agonist, on the Urine and Urothelium of the Rat," Toxicological Sciences 113(2):349-357, Oxford University Press, United States (2010).

European Medicines Agency, "Update on ongoing European review of pioglitazone-containing medicines," retrieved on Nov. 18, 2019, from: https://www.ema.europa.eu/en/news/update-ongoing-european-review-pioglitazon-containing-medicines, dated Jun. 9, 2011, 3 pages.

Yamashita, H., et al., "Thiazolidinedione Derivatives Ameliorate Albuminuria in Streptozotocin-Induced Diabetic Spontaneous Hypertensive Rat," Metabolism 51(4):403-408, W.B. Saunders, United States (2002).

Hsiao, P., et al., "Pioglitazone retrieves hepatic antioxidant DNA repair in a mice model of high fat diet," BMC Mol. Biol. 9(82):1-10, BioMed Central, England (2008).

Collins, A., et al., "Troglitazone inhibits formation of early atherosclerotic lesions in diabetic and nondiabetic low density lipoprotein receptor-deficient mice," Arterioscler. Thromb. Vasc. Biol. 21:365-371, American Heart Association, United States (2001).

Fernandez-Boyanapalli, R., et al., "Pioglitazone restores phagocyte mitochondrial oxidants and bactericidal capacity in chronic granulomatous disease," J. Allergy Clin. Immunol. 135:517-527, American Academy of Allergy, United States (2015).

Heaney, A., et al., "Functional PPAR-gamma receptor is a novel therapeutic target for ACTH-secreting pituitary adenomas," Nature Medicine 8:1281-1287, Nature Publishing Group, England (2002).

Takada, I., and Makishima, M., "PPAR-gamma ligands and their therapeutic applications: a patent review (2008-2014)," Expert Opin. Ther. Patents 25:175-191, Informa, England (2015).

Linker, R., and Lee, D., "Models of autoimmune demyelination in the central nervous system: on the way to translational medicine," Experimental and Translational Stroke Medicine 1(5):1-10, BioMed Central, England (2009).

International Preliminary Report on Patentability (IPRP) for International Application No. PCT/IB2017/057587, European Patent Office, Netherlands, dated Mar. 8, 2019.

Tanis, S.P., et al., "Synthesis and Biological Activity of Metabolites of the Antidiabetic, Antihyperglycemic Agent Pioglitazone," J. Med. Chem. 39(26):5053-5063, American Chemical Society, United States (1996).

Barter, Z.E., et al., "Scaling Factors for the Extrapolation of In Vivo Metabolic Drug Clearance From in Vitro Data: Reaching a Consensus on Values of Human Microsomal Protein and Hepatocellularity Per Gram of Liver," Current Drug Metabolism 8(1):33-45, Bentham Science Publishers Ltd., Netherlands (2007).

Baxter, A.G., "The Origin and Application of Experimental Autoimmune Encephalomyelitis," Nature Reviews Immunology 7(11):904-912, Nature Publishing Group, England (2007).

Callizot, N., et al., "Operational Dissection of β-Amyloid Cytopathic Effects on Cultured Neurons," Journal of Neuroscience Research 91(5):706-716, Wiley Periodicals, Inc., United States (2013).

Fourcade, S., et al., "Mitochondrial Dysfunction and Oxidative Damage Cooperatively Fuel Axonal Degeneration in X-linked Adrenoleukodystrophy," Biochimie 98:143-149, Elsevier Masson SAS, France (2014) (Published online 2013).

Hansen, M.B., et al., "Re-examination and Further Development of a Precise and Rapid Dye Method for Measuring Cell Growth/Cell Kill," Journal of Immunological Methods 119(2):203-210, Elsevier, Netherlands (1989).

International Search Report for International Application No. PCT/EP2015/057224, European Patent Office, Rijswijk, Netherlands, dated Jun. 15, 2015, 4 pages.

Itoh, T. and Yamamoto, K., "Peroxisome Proliferator Activated Receptor γ and Oxidized Docosahexaenoic Acids as New Class of Ligand," Naunyn-Schmiedeberg's Arch. Pharmacol. 377(4-6):541-547, Springer Verlag, Germany (2008).

Kostic, M., et al., "IL-17 and Glutamate Excitotoxicity in the Pathogenesis of Multiple Sclerosis," Scandinavian Journal of Immunology 79(3):181-186, John Wiley & Sons Ltd, England (Mar. 2014).

Lecluyse, E.L. and Alexandre, E., "Isolation and Culture of Primary Hepatocytes from Resected Human Liver Tissue," Methods in Molecular Biology 640:57-82, Humana Press, United States (2010).

Liu, S.-B. and Zhao, M.-G., "Neuroprotective Effect of Estrogen: Role of Nonsynaptic NR2B-containing NMDA Receptors," Brain Research Bulletin 93:27-31, Elsevier Inc., United States (2013) (Published online 2012).

Martinou, J.C., et al., "Cholinergic Differentiation Factor (CDF/LIF) Promotes Survival of Isolated Rat Embryonic Motoneurons in vitro," Neuron 8(4):737-744, Cell Press, United States (1992).

Mosmann, T., "Rapid Colorimetric Assay for Cellular Growth and Survival: Application to Proliferation and Cytotoxicity Assays," Journal of Immunological Methods 65(1-2):55-63, Elsevier Science Publishers B.V., Netherlands (1983).

Pujol, A., et al., "Functional Overlap between ABCD1 (ALD) and ABCD2 (ALDR) Transporters: A Therapeutic Target for X-adrenoleukodystrophy," Human Molecular Genetics 13(23):2997-3006, Oxford University Press, England (2004).

Schlüter, A., et al., "Functional Genomic Analysis Unravels a Metabolic-inflammatory Interplay in Adrenoleukodystrophy," Human Molecular Genetics 21(5):1062-1077, Oxford University Press, England (2012).

Schroeder, K., et al., "Ionworks™M Ht: A New High-throughput Electrophysiology Measurement Platform," Journal of Biomolecu-

(56) References Cited

OTHER PUBLICATIONS lar Screening 8(1):50-64, Sage Publications in association with the Society for Biomolecular Screening, United States (2003).
Singer, C.A., et al., "The Mitogen-Activated Protein Kinase Pathway Mediates Estrogen Neuroprotection after Glutamate Toxicity in Primary Cortical Neurons," *The Journal of Neuroscience* 19(7):2455-2463, Society for Neuroscience, United States (1999).
Office action dated Sep. 2, 2016 in U.S. Appl. No. 15/147,484, inventor Garcia Collazo, A.M.et al., Int'l filing date Apr. 1, 2015, 7 pages.
Sundararajan, S., et al., "PPARγ as a Therapeutic Target in Central Nervous System Diseases," Neurochemistry International 49(2):136-144, Elsevier Ltd, England (2006).
Wang, H. and Sieburth, D., "PKA Controls Calcium Influx into Motor Neurons During a Rhythmic Behavior," *PLoS Genetics* 9(9):e1003831:1-15, Public Library of Science, United States (2013).
Written Opinion for International Application No. PCT/EP2015/057224, European Patent Office, Munich, Germany, dated Jun. 15, 2015, 6 pages.
European Medicines Agency, "Guideline on the investigation of drug interactions, " ema.europa.eu, accessed at http://www.ema.europa.eu/docs/en_GB/document_library/Scientific_guideline/2012/07/WC500129606.pdf, accessed on Mar. 14, 2016, 59 pages (Jun. 2012).
U.S. Department of Health and Human Services, "Guidance for Industry, Drug Interaction Studies—Study Design, Data Analysis, Implications for Dosing, and Labeling Recommendations," fda.gov, accessed at http://www.fda.gov/Drugs/GuidanceComplianceRegulatoryInformation/Guidances/default.htm, accessed on Mar. 14, 2016, 79 pages (Feb. 2012).
Takeda Chemical Industries, "ACTOS™ (Pioglitazone Hydrochloride) Tablets," NDA No. 21-073, drugbank.ca, accessed at http://www.drugbank.ca/system/fda_labels/DB01132.pdf?1265922797, accessed on Mar. 14, 2016, 26 pages (1999).
Extended European Search Report for European Patent Application No. 14382130.4, European Patent Office, Munich, Germany, dated May 28, 2014, 8 pages.
Jaakkola, T., et al., "Pioglitazone is Metabolised by CYP2C8 and CYP3A4 in vitro: Potential for Interactions with CYP2C8 Inhibitors," *Basic & Clinical Pharmacology & Toxicology* 99:44-51, Blackwell Munksgaard, Denmark (2006).
Vidal Medicinal preparations in Russia, "PIOGLITAZONE," vidal.ru, accessed at https://www.vidal.ru/drugs/molecule/1253, accessed on Aug. 11, 2017, 3 pages.
English language machine translation of Vidal Medicinal preparations in Russia, "PIOGLITAZONE," vidal.ru, accessed at https://www.vidal.ru/drugs/molecule/1253, accessed on Aug. 11, 2017, 3 pages.
Web Project Group, "Pioglitazone," webapteka.ru, accessed at http://www.webapteka.ru/drugbase/inn2484.html, accessed on Aug. 11, 2017, 4 pages.
English language machine translation of WEB Project Group, "Pioglitazone," webapteka.ru, accessed at http://www.webapteka.ru/drugbase/inn2484.html, accessed on Aug. 11, 2017, 5 pages.
CINAPS Compound Dossier, "Pioglitazone," pp. 1-21, National Institute of Neurological Disorders and Stroke, United States (Dec. 22, 2009).
Garattini S., "Active Drug Metabolites, An Overview of Their Relevance in Clinical Pharmacokinetics," *Clinical Pharmacokinetics* 10:216-227, ADIS Press Limited, New Zealand (1985).
Goodwin J.T., et al., "In Silico Predictions of Blood-Brain Barrier Penetration: Considerations to 'Keep in Mind'," *J. Pharmacol. Exp. Ther.* 315:477-483, The American Society for Pharmacology and Experimental Therapeutics, United States (2005).
Jhala D.D. et al., "Optimization and Validation of an In Vitro Blood Brain Barrier Permeability Assay," *J. Bioequiv. Availab.* S14:1-5, an open access journal (Jun. 14, 2012).
Leoni A., et al., "Novel thiazole derivatives: a patent review (2008-2012. Part 2)," *Expert Opin. Ther. Patents* 24(7):759-777, Informa UK, Ltd., United Kingdom (Apr. 2014).

Lin Z.L., et al., "Simultaneous determination of pioglitazone and its two active metabolites in human plasma by LC-MS/MS," *Journal of Pharmaceutical and Biomedical Analysis* 33:101-108, Elsevier B.V., Netherlands (2003).
Lin J.H., et al., "Blood-Brain Barrier Permeability and in Vivo Activity of Partial Agonists of Benzodiazepine Receptor: A Study of L-663,581 and its Metabolites in rats," *J. Pharmacol. Exp. Ther.* 271:1197-1202, The American Society for Pharmacology and Experimental Therapeutics, United States (1994).
Pajouhesh H. et al., "Medicinal Chemical Properties of Successful Central Nervous System Drugs," *NeuroRx®: The Journal of the American Society for Experimental NeuroTherapeutics* 2(4):541-553, The American Society for Experimental Neurotherapeutics, Inc., United States (2005).
Pardridge V.M., "Blockade of BBB transport of lipid-soluble molecules" in *Brain drug targeting: The future of brain drug development*, pp. 48-49, Cambridge University Press, United Kingdom (2001).
"The ICD-10 Classification of Mental and Behavioral Disorders, Diagnostic criteria for research," pp. 1-268, World Health Organization, Geneva (1993).
Pankevich, D. E., et al., "Improving and Accelerating Drug Development for Nervous System Disorders," *Neuron* 84:546-553, Elsevier Inc., United States (2014).
Office Action dated May 14, 2018, in U.S. Appl. No. 15/725,950, Collazo et al., filed Oct. 5, 2017, 9 pages.
Extended European Search Report mailed for EP Appl. No. 18173541.6, European Patent Office, Munich, Germany, 9 pages, completed Jun. 19, 2018.
Choi, D. W., et al., "Glutamate Neurotoxicity in cortical Cell Culture," *The Journal of Neuroscience* 7(2):357-368, Society for Neuroscience, United States (1987).
Lesuisse, C. and Martin, L. J., "Long-Term Culture of Mouse Cortical Neurons as a Model for Neuronal Development, Aging, and Death," *J. Neurobiol.* 51:9-23, Wiley Periodicals, Inc., Unites States (2002).
Lewerenz, J. and Maher, P., "Chronic Glutamate Toxicity in Neurodegenerative Diseases—What is the Evidence?," *Frontiers in Neuroscience* 9:469, pp. 1-20, doi: 10.3389/fnins.2015.00469, United States (Dec. 2015).
Lipton, S. A. and Rosenberg, P. A., "Mechanisms of a Disease—Excitatory Amino Acids as a Final Common Pathway for Neurologic Disorders," *The New England Journal of Medicine* 330(9):613-622, Massachusetts Medical Society, United States (1994).
Frisoni, G.B., et al., "Multiple Sclerosis and Alzheimer Disease through the Looking Glass of MR Imaging," Am J. Neuroradiol 26:2488-2491, Society of Neuroradiology, United States (2005).
United States Patent and Trademark Office, "Comments on the USPTO's Guidance for Determining Subject Matter Eligibility of Claims Reciting or Involving Laws of Nature, Natural Phenomena, & Natural Products," 5 pages, May 8, 2014.
Yamashita, K., et al., "High-performance liquid chromatographic determination of pioglitazone and its metabolites in human serum and urine," Journal of Chromatography B 677:141-146, Elsevier Science B.V., Netherlands (1996).
Boden, G., et al., "Free fatty acids in obesity and type 2 diabetes: defining their role in the development of insulin resistance and β-cell dysfunction," European Journal of Clinical Investigation 32 (Suppl. 3):14-23, Blackwell Sciences, L.T.D., United States (2002).
McCall, A., "The Impact of Diabetes on the CNS," Diabetes 41:557-570, American Diabetes Association, United States (1992).
Ragheb, R., et al., "Mechanism of Fatty Acid-Induced Insulin Resistance in Muscles and Liver," J. Diabetes Metab 2(4): 1-5, Longdom Publishing, Spain (2011).
Roden, M., et al., "Mechanism of Free Fatty Acid-induced Insulin Resistance in Humans," J. Clin Invest 97(12):2859-2865, American Society for Clinical Investigation, United States (1996).
Watkins, P.J., et al., "Diabetes mellitus and the nervous system," J. Neurol Neurosurg Psychiatry 65:620-632, Neurology and Medicine, United States (1998).

(56) References Cited

OTHER PUBLICATIONS

Backman, J.T., et al., "Role of Cytochrome P450 2C8 in Drug Metabolism and Interactions," Pharmacol Rev 68(1):168-241, American Society for Pharmacology and Experimental Therapeutics, United States (Jan. 2016).

Anonymous, "Drug Metabolism—The Importance of Cytochrome P450 3A4," Prescriber Update 35(1):4-6, MedSafe, New Zealand (Mar. 2014).

* cited by examiner

5-[[4-[2-[5-(1-HYDROXYETHYL)PYRIDIN-2-YL]ETHOXY]PHENYL]METHYL]-1,3-THIAZOLIDINE-2,4-DIONE FOR TREATING NONALCOHOLIC FATTY LIVER DISEASE

CROSS-REFERENCE TO RELATED APPLICATION

This application is a 35 U.S.C. § 371 National Phase Application of International Application No. PCT/IB2017/057587, filed Dec. 1, 2017, which claims priority to European Application No. EP16382584.7, filed on Dec. 1, 2016, the entirety of which is incorporated by reference herein.

FIELD OF DISCLOSURE

The present disclosure relates to the use of 5-[[4-[2-[5-(1-hydroxyethyl)pyridin-2-yl]ethoxy]phenyl]methyl]-1,3-thiazolidine-2,4-dione and its pharmaceutically acceptable salts in the treatment or prevention of a disease selected from the group consisting of nonalcoholic fatty liver disease, nonalcoholic steatohepatitis, a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease. Specifically, the present disclosure relates to the use of 5-[[4-[2-[5-(1-hydroxyethyl)pyridin-2-yl]ethoxy]phenyl]methyl]-1,3-thiazolidine-2,4-dione and its pharmaceutically acceptable salts in the treatment or prevention of nonalcoholic fatty liver disease, including nonalcoholic steatohepatitis.

BACKGROUND

Metabolic syndrome is a cluster of metabolic abnormalities that identifies people at risk of diabetes and cardiovascular disease. Glucose and triglycerides are overproduced by the liver in subjects having metabolic syndrome. The liver is therefore a key determinant of metabolic abnormalities. The prevalence of both metabolic syndrome and nonalcoholic fatty liver disease ("NAFLD") increases with obesity. Other acquired causes for both disorders include excessive intake of simple sugars and physical inactivity. Both disorders predict type 2 diabetes, cardiovascular disease, nonalcoholic steatohepatitis ("NASH"), and hepatocellular carcinoma. Because metabolic syndrome can be defined in many different ways, NAFLD might be a more direct predictor of these diseases. Half of people with NAFLD carry at least one variant (G) allele at rs738409 in the PNPLA3 gene, which is associated with high liver fat content. Steatosis in PNPLA3-associated NAFLD is not accompanied by features of metabolic syndrome. All forms of NAFLD increase the risk of NASH, cirrhosis, and hepatocellular carcinoma.

NAFLD encompasses a spectrum of diseases ranging from isolated hepatic steatosis to NASH, the more aggressive form of fatty liver disease that may progress to cirrhosis and cirrhosis-related complications, including hepatocellular carcinoma ("HCC"). NAFLD and NASH are characterized by excessive fat accumulation in the form of triglycerides (steatosis) in the liver in patients who do not abuse alcohol. NASH is found in a subset of NAFLD patients who have, in addition to excess fat, evidence of characteristic hepatocellular injury and necroinflammatory changes. NAFLD is a major form of chronic liver disease that is not associated with significant alcohol consumption. NAFLD is a condition where excessive fat accumulates in the form of triglycerides (steatosis) in the liver, and is histologically characterized by more than 5% hepatic triglyceride accumulation, resulting in steatosis and hepatic inflammation. The prevalence of NAFLD, including NASH, is also increasing in parallel with the growing epidemics of obesity and diabetes. However, the causal relationships between obesity and/or diabetes, and NASH or liver tumorigenesis have not yet been clearly elucidated. Researchers have proposed that NAFLD may result as a consequence of multiple parallel hits, such as gut- and adipose tissue-derived factors and that NAFLD is a complex, polygenic disease. Animal models of NAFLD/NASH have provided crucial information, not only for elucidating the pathogenesis of NAFLD/NASH, but also for examining therapeutic effects of various agents. Different diets have been used to produce hepatic steatosis and NASH in experimental animals, such as a high-fat diet or methionine choline deficient diet. Several studies have shown that long-term high-fat or methionine choline deficient diet loading, which can induce obesity and insulin resistance, can also induce NASH and liver tumorigenesis in C57BL/6J mice. (See, e.g., Nakamura et al. *Int. J. Mol. Sci.* 14: 21240-21257 (2013) and Imajo et al., *Int. J. Mol. Sci.* 14: 21833-21857 (2013).)

NAFLD is associated with cardiometabolic risk factors and metabolic syndrome, and is the most common chronic liver disease among adults in developed countries. It has been estimated that as many as 30% of adults in the USA and other Western countries have NAFLD; the prevalence increases to more than two-thirds in obese subjects. On the other hand, NASH may be present in up to 3% of the general population. In addition to hepatic complications, patients with NAFLD are at an increased risk for cardiovascular diseases. (See, e.g., Nakamura et al., *Int. J Mol. Sci.* 14: 21240-21257 (2013)).

NASH is a form of metabolic liver disease in which fatty change (steatosis) is associated with lobular inflammation, hepatocyte injury, and/or hepatic fibrosis. It comprises a pathogenic link in the chain of NAFLD that extends from bland steatosis to some cases of "cryptogenic cirrhosis." NAFLD and NASH are usually hepatic manifestations of the insulin resistance (or metabolic) syndrome, but the factors that transform steatosis to NASH remain unclear. Standardized definitions, however, are lacking, particularly for what pathology is encompassed by "significant steatohepatitis." NAFLD/NASH is the most common type of liver disease in affluent societies. NASH typically causes no symptoms. NASH patients typically have an increased neutrophil-to-lymphocyte ratio ("NLR") as compared to patients without NASH. The NLR, therefore, is a marker for predicting steatohepatitis in patients with NAFLD. See, e.g., Alkhouri et al., *Liver Int.* 32(2):297-302 (2012). When present, clinical features such as fatigue, hepatomegaly, and aching hepatic discomfort are non-specific. In 20-25% of cases, NASH may progress to advanced stages of hepatic fibrosis and cirrhosis; liver failure then becomes the most common cause of death, and HCC may occasionally occur. Correction of insulin resistance by dietary measures and increased physical activity (lifestyle intervention) is a logical approach to prevent or reverse early NASH, and modest weight reduction can normalize liver test abnormalities. Drug therapy aimed at reversing insulin resistance, correcting diabetes and lipid disorders, or providing "hepatocellular protection" has been shown to improve liver tests in short-term small studies, but larger randomized controlled trials are needed to establish whether any of these approaches arrest progression of hepatic fibrosis and prevent liver complications, and at what stage interventions are cost-effective. (See, e.g., Farrell et al., *Introduction to NASH and*

*Related Disorders: Chapter 1 Overview: an introduction to NASH and related fatty liver disorders* (2007)).

There is not a definitive and effective treatment strategy for NAFLD and NASH. Pioglitazone has been used to treat NAFLD and NASH, but due to unwanted side effects, is not a suitable candidate for treatment (See, e.g., Kus et al., *PLoS ONE* 6(11): e27126 (2011) and Belfort et al., *The New England Journal of Medicine* 355(22):2297-2307 (2006)). There is currently no cure for NASH, and the current therapies aim to control the conditions that are associated with NASH: obesity, diabetes, and hyperlipidemia. Several drugs are available for people with insulin resistance, and they are being studied for NASH, such as pioglitazone. However, their role has not yet proven.

Pioglitazone is a drug marketed for use in the treatment of diabetes mellitus type 2. Pioglitazone is a potent agonist for peroxisome proliferator-activated receptor-gamma (PPAR-γ). But pioglitazone has been associated with unwanted side effects including the potential for drug to drug interactions, cardiovascular effects, fluid retention, weight gain, and bladder cancer (See, e.g., Kus et al., *PLoS ONE* 6(11): e27126 (2011)). High doses and/or chronic administration of pioglitazone are therefore undesirable as high systemic exposure would be likely to result in serious side effects.

Pioglitazone is a "dirty" drug which is converted to many metabolites in vivo. The metabolic pathway of pioglitazone after oral administration has been studied in several animal species and in humans, and the metabolites have been described in the literature (See, e.g., Sohda et al., *Chem. Pharm. Bull.* 43(12):2168-2172 (1995) and Maeshiba et al., *Arzneim.-Forsch Drug Res.* 47(I):29-35 (1997). At least six metabolites have been identified, named M-I to M-VI. Among these metabolites, M-II, M-III, and M-IV show some pharmacological activity but are less active than pioglitazone in diabetic preclinical models. 5-[[4-[2-[5-(1-hydroxyethyl)pyridin-2-yl]ethoxy]phenyl]methyl]-1,3-thiazolidine-2,4-dione has shown to be effective in the treatment of central nervous system diseases (See WO 2015/150476 A1).

There is an urgent need for new treatments for NAFLD and NASH.

SUMMARY

The present disclosure provides an improved method of treating or preventing NAFLD, NASH, a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease, and specifically NAFLD and NASH. The inventors have surprisingly found that compounds of formula (1), and salts thereof, exhibit an improved safety profile when compared to another 2,4-thiazolidinedione compound, pioglitazone. Specifically, compounds of formula (1), and salts thereof, have been found to exhibit a lower risk of drug to drug interactions and a lower risk of bladder cancer than pioglitazone, and to exhibit a lower pharmacokinetic (PK) variability in humans than pioglitazone.

Thus the present disclosure provides a method of treating or preventing nonalcoholic fatty liver disease (NAFLD), and specifically nonalcoholic steatohepatitis (NASH), wherein the method comprises administering to a subject in need thereof a compound of formula (1)

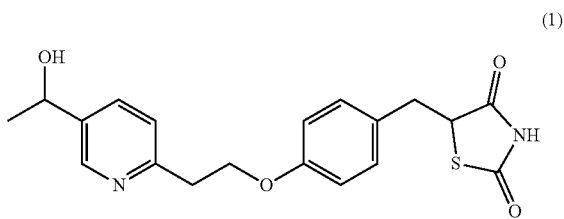 [SMILES: CC(O)c1ccc(CCOc2ccc(CC3SC(=O)NC3=O)cc2)nc1]

(1)

or a pharmaceutically acceptable salt thereof, in an amount effective to treat or prevent nonalcoholic fatty liver disease. In an embodiment the compound of formula (1) is one or more of compounds: (2) (R)-5-[[4-[2-[5-(R)-(1-hydroxyethyl)pyridin-2-yl]ethoxy]phenyl]methyl]-1,3-thiazolidine-2,4-dione; (3) (R)-5-[[4-[2-[5-(S)-(1-hydroxyethyl)pyridin-2-yl]ethoxy]phenyl]methyl]-1,3-thiazolidine-2,4-dione; (4) (S)-5-[[4-[2-[5-(R)-(1-hydroxyethyl)pyridin-2-yl]ethoxy]phenyl]methyl]-1,3-thiazolidine-2,4-dione; or (5) (S)-5-[[4-[2-[5-(S)-(1-hydroxyethyl)pyridin-2-yl]ethoxy]phenyl]methyl]-1,3-thiazolidine-2,4-dione; or a pharmaceutically acceptable salt thereof. In one embodiment, no more than 1% of the total number of hydrogen atoms per mole of the compound of formula (1) are in the form of the $^2$H isotope.

In another embodiment, the method of treatment or prevention comprises administering a mixture of two or more of compounds selected from the group consisting of (2), (3), (4), and (5), or a pharmaceutically acceptable salt thereof, wherein the mixture is optically active. In one embodiment, compounds (2) and (3) are administered. In another embodiment, compounds (4) and (5) are administered. In another embodiment, compounds (2) and (4) are administered. In another embodiment, compounds (3) and (5) are administered.

In one aspect of the disclosure, the nonalcoholic fatty liver disease is nonalcoholic steatohepatitis. In another embodiment, the method further comprises administering an additional therapeutic agent. In another embodiment, the compound of formula (1), or a pharmaceutically acceptable salt thereof, is administered to the subject in an oral dosage form, such as a tablet, a capsule, a pill, a plurality of granules, an oral solution or an oral suspension.

The present disclosure also provides a compound of formula (1), or a pharmaceutically acceptable salt thereof, for use in the treatment or prevention of alcoholic fatty liver disease, and specifically nonalcoholic steatohepatitis, the compound of formula (1) having the structure:

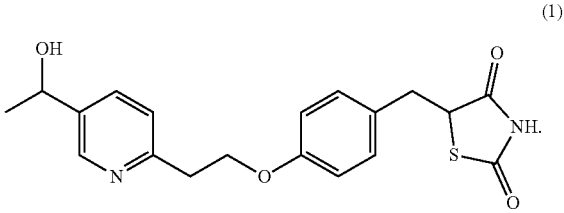 [SMILES: CC(O)c1ccc(CCOc2ccc(CC3SC(=O)NC3=O)cc2)nc1]

(1)

In another aspect, the present disclosure provides a pharmaceutical composition, comprising the compound of formula (1), or a pharmaceutically acceptable salt thereof, for use in the treatment or prevention of nonalcoholic fatty liver disease, and specifically nonalcoholic steatohepatitis. According to another aspect, the present disclosure provides use of a compound of formula (1), or a pharmaceutically acceptable salt thereof, in the manufacture of a medicament for the treatment or prevention of nonalcoholic fatty liver disease, and specifically nonalcoholic steatohepatitis.

In another aspect, the present disclosure provides a method of treating or preventing a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease, comprising administering to a subject in need thereof a compound of formula (1)

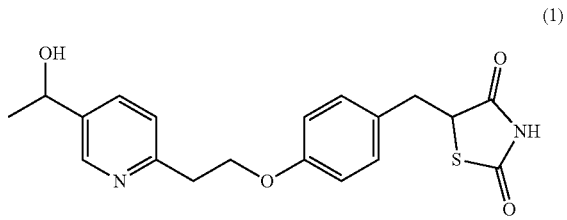 [SMILES: CC(O)c1ccc(CCOc2ccc(CC3SC(=O)NC3=O)cc2)nc1]

(1)

or a pharmaceutically acceptable salt thereof, in an amount effective to treat or prevent a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

DETAILED DESCRIPTION

Figure 1:
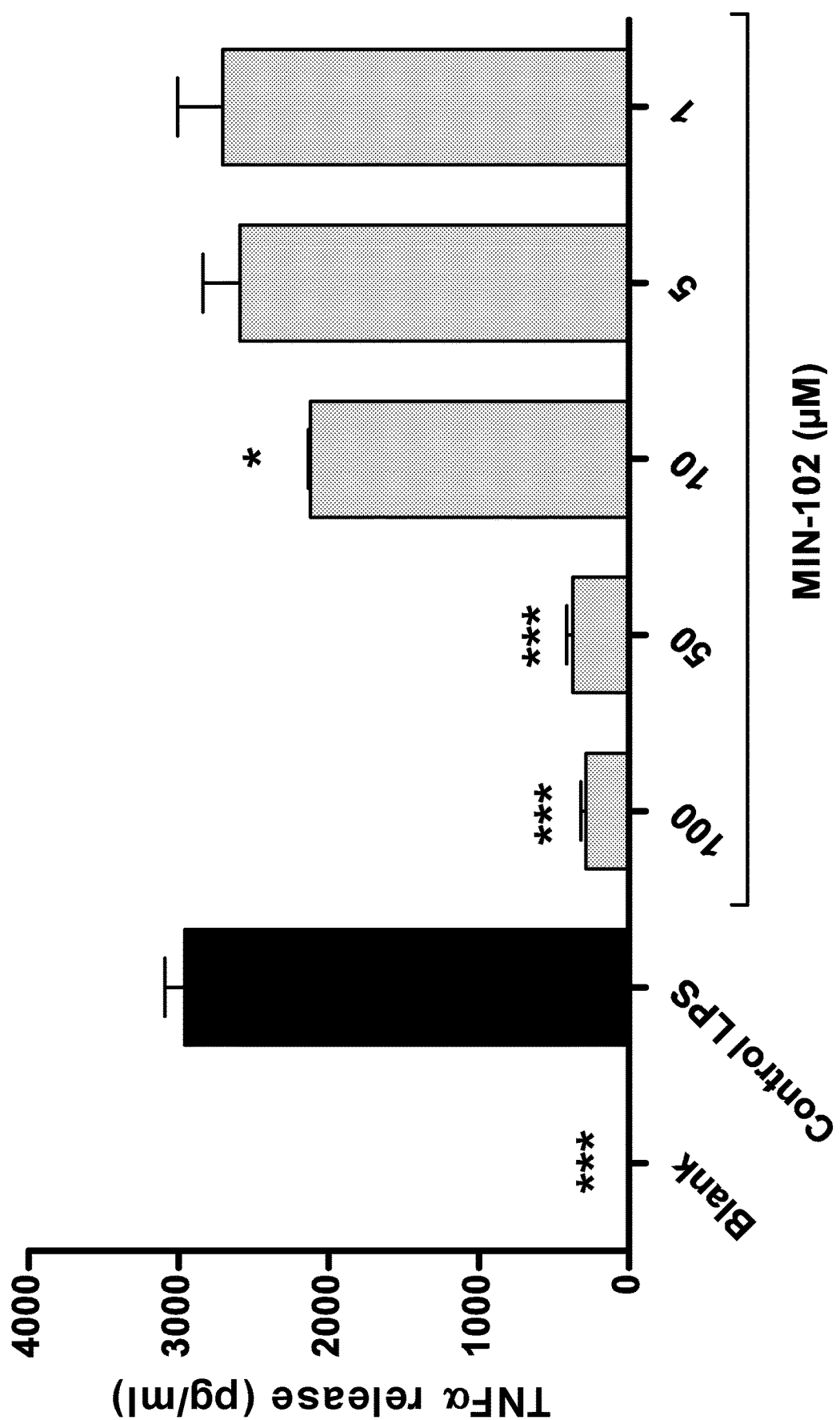
FIG. 1 represents a comparison of the anti-inflammatory effects of MIN-102 in an in vitro lipopolysaccharide-induced inflammation model.

NASH is an emerging disease belonging to the NAFLD spectrum, and may progress to fibrosis and cirrhosis of the liver. Currently, there is no definitive and effective treatment strategies identified to treat NASH.

In one aspect, the present disclosure is drawn to a method of treating or preventing nonalcoholic fatty liver disease, comprising administering to a subject in need thereof an effective amount of a compound of formula (1) or a pharmaceutically acceptable salt thereof, in an amount effective to treat or prevent nonalcoholic fatty liver disease. In one embodiment, NAFLD is NASH. Also disclosed is a compound of formula (1), or a pharmaceutically acceptable salt thereof, for use in the treatment or prevention of nonalcoholic fatty liver disease. In one embodiment, NAFLD is NASH. Also disclosed is use of a compound of formula (1), or a pharmaceutically acceptable salt thereof, in the manufacture of a medicament for the treatment or prevention of nonalcoholic fatty liver disease. In one embodiment, NAFLD is NASH.

The present disclosure is also drawn to a method of treating or preventing a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease, comprising administering to a subject in need thereof a compound of formula (1) or a pharmaceutically acceptable salt thereof, in an amount effective to treat or prevent a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

The present disclosure is also drawn to a method of treating or preventing a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease, comprising administering to a subject in need thereof a dosage form comprising an effective amount of a compound of formula (1) or a pharmaceutically acceptable salt thereof.

In an embodiment, the skin disease is one or more of vitiligo, psoriasis, pruritus, acne, or dermatitis. In an embodiment, the inflammation and autoimmune disease is one or more of inflammatory bowel disease, lupus, arthritis, or asthma. In an embodiment, the inflammatory respiratory disease is chronic obstructive pulmonary disorder.

It has been unexpectedly discovered that compounds of formula (1)

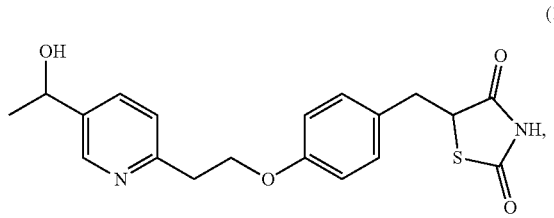

(1)

having the chemical name 5-[[4-[2-[5-(1-hydroxyethyl)pyridin-2-yl]ethoxy]phenyl]methyl]-1,3-thiazolidine-2,4-dione (also called as 5-(4-(2-(5-(1-hydroxyethyl)pyridine-2-yl)ethoxy)benzyl)thiazolidine-2,4-dione, hydroxypioglitazone, hydroxy pioglitazone, or M-IV), and pharmaceutically acceptable salts thereof, collectively referred to herein as "Compounds of the Disclosure" (each is individually referred to hereinafter as a "Compound of the Disclosure") are useful in a method of treating or preventing NAFLD and NASH, providing a safe method to the patients with minimal or reduced side-effects. The inventors have found that Compounds of the Disclosure exhibit an overall superior safety profile, as compared to pioglitazone. This is especially useful in the treatment of patients requiring chronic treatment, such as those suffering from NAFLD or NASH. This profile is also useful in the treatment of patients requiring treatment for a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

Pioglitazone has been tested for treating NASH (See, e.g., Belfort et al., N. Engl. J. Med. 355(22):2297-2307 (2006); Sanyal et al., N. Engl. J. Med. 362(18):1675-1685 (2010)). However, chronic treatment with pioglitazone is associated with unwanted side effects including the potential for drug to drug interactions, cardiovascular effects, fluid retention, weight gain, and bladder cancer. Chronic administration and/or high doses of pioglitazone are therefore undesirable as high systemic exposure would be likely to result in serious side effects. Warnings about the use of pioglitazone and the risk of bladder cancer led to the withdraw for the future use of the drug in France and Germany (See, e.g., "Update on ongoing European review of pioglitazone-containing medicines," European Medicines Agency (Jun. 9, 2011)).

In addition, pioglitazone has a variety of possible drug-drug interactions:

Potential interactions with modulators of 2C8 with fibrates (PPAR alpha agonists such as gemfibrozil used as lipid lowering); anticancerigens (Sorafenib, Paclitaxel); statins (Cerivastatin); antibiotics (Rifampin and Trimethorpim);

Potential interactions with modulators of 2C9 with Leflunomide (rheumatoid arthritis); Teriflunomide (Multiple sclerosis) and Nateglinide (diabetes); and Potential interactions with modulators of 3A4 with COMT inhibitors (Entacapone); MAO B inhibitors (Selegiline); Modafinil; acetylcholinesterase inhibitors (Galantamine); donepezil; immunomodulators (Fluoxetine, Tacrolimus, Sirolimus).

Compounds of the Disclosure have been shown to exhibit a lower risk of drug to drug interactions and a lower risk of bladder cancer. In addition, Compounds of the Disclosure have been shown to exhibit a lower PK variability in humans than pioglitazone. Compounds of the Disclosure also potentially offer an advantage for those individuals that present a polymorphism in genes that directly affect the metabolism of pioglitazone.

Lower risk of epithelium hyperplasia (bladder cancer): The presence of epithelium hyperplasia in rats after a long treatment has been proved a good predictive marker for the risk of cancer of PPAR gamma agonists. The mechanism of action of this epithelium hyperplasia may be independent of PPAR gamma agonism.

Current data suggest that treatment with a Compound of the Disclosure shows lower incidence of epithelium hyperplasia in rats, and therefore, a lower potential for bladder cancer. Example 1 shows that epithelium hyperplasia, which is a predictive marker of a possible risk of bladder cancer, was only observed in the pioglitazone group.

Lower potential for drug-drug interaction: Drug-drug interactions can lead to changes in systemic exposure, resulting in variations in drug response of the co-administered drugs. In addition to co-administration of other drugs, concomitant ingestion of dietary supplements, citrus fruit, or fruit juice could also alter systemic exposure of drugs, thus leading to adverse drug reactions or loss of efficacy. Therefore, it is important to evaluate potential drug interactions prior to market approval as well as during the postmarketing period.

As indicated in the Examples, the advantages of Compounds of the Disclosure over pioglitazone are related to the potential drug-drug interactions of pioglitazone with substrates, inhibitors, or inducers of CYP2C8, CYP2C9, CYP3A4, and CYP2B6. As shown in the Examples, 5-[[4-[2-[5-(1-hydroxyethyl)pyridin-2-yl]ethoxy]phenyl]methyl]-1,3-thiazolidine-2,4-dione does not cause remarkable reversible or time-dependent inhibition towards major CYP enzymes. Furthermore, 5-[[4-[2-[5-(1-hydroxyethyl)pyridin-2-yl]ethoxy]phenyl]methyl]-1,3-thiazolidine-2,4-dione is cleaner than pioglitazone as a potential CYP inducer based on experimental data with CYP3A4 and CYP2B6.

Lower PK variability in humans: As indicated in Example 7, the response to pioglitazone in NASH patients is concentration-dependent. See, Kawaguchi-Suzuki et al., Aliment. Pharmacol. Ther. 46(1):56-61 (2017). Due to its PK variability, pioglitazone was not seen effective in all NASH patients, and higher doses would be required to ensure its efficacy in all treated NASH patients. Higher doses of pioglitazone would increase the risk of developing adverse events. Compounds of the Disclosure have a lower PK variability and therefore treatment with Compounds of the Disclosure is safer than treatment with pioglitazone.

The compound of formula (1), 5-[[4-[2-[5-(1-hydroxyethyl)pyridin-2-yl]ethoxy]phenyl]methyl]-1,3-thiazolidine-2,4-dione, has two chiral centres. One of them is the carbon atom in the 5-position of the thiazolidine-dione ring and the other asymmetric atom is at position 1 of the hydroxyethyl group as shown by the arrows:

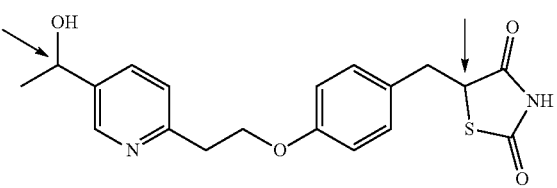 [SMILES: CC(O)c1ccc(CCOc2ccc(CC3SC(=O)NC3=O)cc2)nc1]

As used herein the term "compound of formula (1)" is used to designate all possible stereoisomers, including enantiomers and diastereomers, and mixtures including racemic mixtures thereof.

In one embodiment, the compound of formula (1) is selected from the group consisting of:

Compound (2) (R)-5-[[4-[2-[5-(R)-(1-hydroxyethyl)pyridin-2-yl]ethoxy]phenyl]methyl]-1,3-thiazolidine-2,4-dione

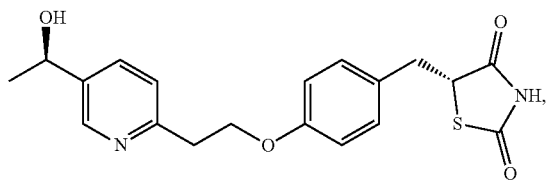 [SMILES: C[C@@H](O)c1ccc(CCOc2ccc(C[C@H]3SC(=O)NC3=O)cc2)nc1]

Compound (3) (R)-5-[[4-[2-[5-(S)-(1-hydroxyethyl)pyridin-2-yl]ethoxy]phenyl]methyl]-1,3-thiazolidine-2,4-dione

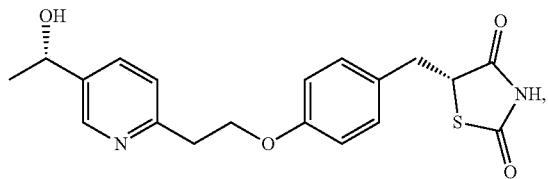 [SMILES: C[C@H](O)c1ccc(CCOc2ccc(C[C@H]3SC(=O)NC3=O)cc2)nc1]

Compound (4) (S)-5-[[4-[2-[5-(R)-(1-hydroxyethyl)pyridin-2-yl]ethoxy]phenyl]methyl]-1,3-thiazolidine-2,4-dione

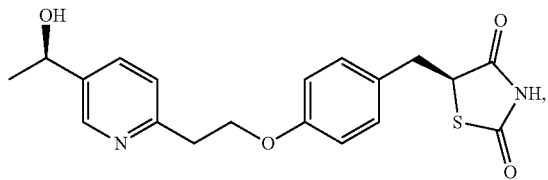 [SMILES: C[C@@H](O)c1ccc(CCOc2ccc(C[C@@H]3SC(=O)NC3=O)cc2)nc1]

Compound (5) (S)-5-[[4-[2-[5-(S)-(1-hydroxyethyl)pyridin-2-yl]ethoxy]phenyl]methyl]-1,3-thiazolidine-2,4-dione

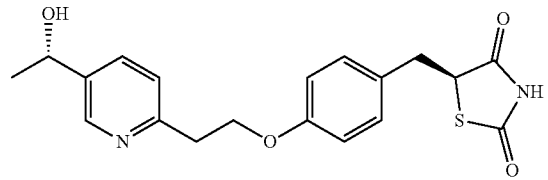 [SMILES: C[C@H](O)c1ccc(CCOc2ccc(C[C@@H]3SC(=O)NC3=O)cc2)nc1]

or a pharmaceutically acceptable salt thereof.

Although compounds (2) to (5) have been prepared as described in WO 2015/150476 A1 and isolated, their absolute (R/S) configuration has not yet been determined. The retention time of each enantiomer has been measured by chiral HPLC.

Reference to compounds (1) to (5) in the present disclosure is intended to designate compounds (1) to (5) having hydrogen atoms which are predominantly in the form of its isotope $^1H$, i.e. no more than 1% of the total number of hydrogen atoms per mole of compound are in the form of the $^2H$ isotope (deuterium). In one embodiment, no more than 0.015% (which is the natural abundance of deuterium) of the total number of hydrogen atoms per mole of compound are in the form of the $^2H$ isotope (deuterium).

In one embodiment, the patient can be administered a mixture comprising a non-equimolar amount of each compound (2), (3), (4), and (5), or a pharmaceutically acceptable salt thereof. In another embodiment, the mixture comprises each of compound (2), (3), (4), and (5), or a pharmaceutically acceptable salt thereof, in an amount of 20% 10% w/w. In another embodiment, the mixture comprises each of compound (2), (3), (4), and (5), or a pharmaceutically acceptable salt thereof, in an amount of 25%±5% w/w.

In another embodiment, the patient can be administered a mixture comprising each compound (2), (3), (4), and (5), or a pharmaceutically acceptable salt thereof, wherein the mixture comprises an enantiomeric excess of one or more of compound (2), (3), (4), and (5). In another embodiment, the patient can be administered a mixture comprising an equimolar amount of each compound (2), (3), (4), and (5), or a pharmaceutically acceptable salt thereof, i.e., each compound in an amount of 25% w/w.

In one embodiment, the patient can be administered a mixture of two or more compounds selected from the group consisting of compound (2), compound (3), compound (4), and compound (5), or a pharmaceutically acceptable salt thereof, wherein the mixture is optically active. In another embodiment, the mixture comprises two or more compounds selected from the group consisting of:
    (a) the compound (2) and the compound (3);
    (b) the compound (4) and the compound (5);
    (c) the compound (2) and the compound (4); and
    (d) the compound (3) and the compound (5),
or a pharmaceutically acceptable salt thereof.

In another embodiment, the patient is administered the mixture (c) or the mixture (d).

In another embodiment, the patient is administered a mixture consisting essentially of:
    (a) the compound (2) and the compound (3), or a pharmaceutically acceptable salt thereof, as the active agents;
    (b) the compound (4) and the compound (5), or a pharmaceutically acceptable salt thereof, as the active agents;
    (c) the compound (2) and the compound (4), or a pharmaceutically acceptable salt thereof, as the active agents; and
    (d) the compound (3) and the compound (5), or a pharmaceutically acceptable salt thereof, as the active agents.

In another embodiment of the mixtures (a) to (d) mentioned above, the two compounds mentioned in each one of the mixtures are present in equimolar quantities. Said mixtures may comprise also minor amounts (e.g., less than 10 wt. %, less than 3 wt. %, less than 1 wt. %, and less than 0.1 wt. % of another stereoisomer of formula (1)). Said mixtures can also be enantiomerically enriched with respect to one or more compounds (2), (3), (4), and (5).

Another aspect of the disclosure, suitable pharmaceutically acceptable salts of Compounds of the Disclosure include, for example, pharmaceutically acceptable acid addition salts of the Compounds of the Disclosure can be prepared from the following acids, including without limitation, formic, acetic, propionic, benzoic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, xinafoic, tartaric, trifluoroacetic, pamoic, propionic, anthranilic, mesylic, napadisylate, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. In an embodiment, the pharmaceutically acceptable salts include the salts of hydrochloric acid and hydrobromic acid. In an embodiment, the pharmaceutically acceptable salt includes the salt of the hydrochloric acid.

Compounds of the Disclosure can be prepared by any suitable method known in the art, such as by the processes described in WO 2015/150476 A1. 5-[[4-[2-[5-(1-hydroxyethyl)pyridin-2-yl]ethoxy]phenyl]methyl]-1,3-thiazolidine-2,4-dione is also commercially available from, for example, Santa Cruz Biotechnology and Toronto Research Chemicals (Toronto, Ontario, Canada).

Various examples and embodiments of the inventive subject matter disclosed here are possible and will be apparent to a person of ordinary skill in the art, given the benefit of this disclosure. In this disclosure reference to "some embodiments," "certain embodiments," "certain exemplary embodiments," and similar phrases each means that those embodiments are non-limiting examples of the inventive subject matter, and there are alternative embodiments which are not excluded.

The articles "a," "an," and "the" are used herein to refer to one or to more than one (i.e., to at least one) of the grammatical object of the article. By way of example, "an element" means one element or more than one element.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also contemplated and within the scope of this disclosure.

The term "ameliorate" in the context of this present disclosure is understood as meaning any improvement on the situation of the patient treated.

The term "bid administration" or "BID" means twice daily administration of a therapeutic.

The term "SAD" means a single oral dose administration of a therapeutic.

In the present disclosure, each of the terms "compound of formula (1)", "hydroxypioglitazone," "hydroxy pioglitazone (M-IV)," "hydroxy pioglitazone," and "5-[4-[2-(5-(1-hydroxyethyl)-2-pyridinyl)ethoxy]benzyl]-2,4-thiazolidinedione" refer to 5-[[4-[2-[5-(1-hydroxyethyl)pyridin-2-yl]ethoxy]phenyl]methyl]-1,3-thiazolidine-2,4-dione, which has the structure depicted above, and any stereoisomer thereof. The term "MIN-102" refers to the hydrochloride salt of racemic 5-[[4-[2-[5-(1-hydroxyethyl)pyridin-2-yl]ethoxy]phenyl]methyl]-1,3-thiazolidine-2,4-dione.

By an "effective" amount or a "therapeutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The term "treatment" or "to treat" in the context of this specification means to ameliorate or eliminate the disease or one or more symptoms associated with said disease. "Treatment" also encompasses ameliorating or eliminating the physiological sequelae of the disease.

The term "pharmaceutically acceptable salt" refers to salts prepared from pharmaceutically acceptable inorganic and organic acids.

The term "prevention" or "to prevent" refers to the reduction in the risk of acquiring or developing a given disease or disorder, or the reduction or inhibition of the recurrence or a disease or disorder.

As used herein, the phrase "PK variability" or "pharmacokinetic variability" refer to inter-individual variations of a drugs pharmacokinetic parameters, resulting in different plasma concentration-time profiles after administration of the same dose to different patients.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

Methods of Treatment or Prevention

For use in the treatment of NAFLD, NASH, and the other diseases and disorders described herein, the activities of the Compounds of the Disclosure can be determined by use of the appropriate in vitro and in vivo assays.

The utility of the compound of formula (1) in the present method, including stereoisomers (2) to (5), mixtures (a) to (d), and pharmaceutically acceptable salts thereof can be demonstrated in appropriate in vitro or in vivo assays.

According to one NASH model in mice (See Verdelho Machado et al., *PlosOne* May 27:10(5):e0127991 (2015)), male C57BL/6 inbred mice, aged 8 weeks, were obtained from Charles River, France. During the acclimation phase, standard (control chow) diet (RM1 (E) 801492, SDS) and tap water was provided ad libitum. Mice were then fed a Methionine Choline Deficient (MCD) diet (ref #A02082002B from Research Diets, USA) supplemented without or with the test item, provided ad libitum. All procedures were performed in accordance with the *Guide for the Care and Use of Laboratory Animals* (revised 1996 and 2011, 2010/63/EU) and French laws. 20 animals were housed in ventilated and enriched housing cages (310×125× 127 mm$^3$) throughout the experimental phase. Animals' cages litters were changed at least once a week. They were housed in groups of 10 animals during the whole study, on a normal 12 hours light cycle (at 08:00 pm lights off), 22±2° C. and 50±10% relative humidity.

After the acclimation period, mice (n=20) were weighed and randomized into 2 homogenous treatment groups based on body weight (n=10/group), put on a MCD diet, and treated BID orally with vehicle or MIN-102 for 7 weeks. Body weight was measured 3 times/week until the end of the experimental phase. At 7 weeks of diet/treatment, mice were weighed and treated at ~08:00 am in the morning, then bled (maximal volume/EDTA) at ~1:00 pm. Plasma was then immediately isolated and stored at ~80° C. prior to assay plasma ALT and AST. The plasma volume left over was stored at ~80° C. for eventual additional analysis.

After blood collection, mice were sacrificed by cervical dislocation under isoflurane anesthesia and exsanguinated with sterile saline. Liver was collected and weighed. A ~20 mg liver sample (weight recorded) was dissected for hepatic total cholesterol and triglycerides levels. A 0.5 cm$^3$ liver sample was frozen in isopentane for oil red O staining. A 0.5 cm$^3$ liver sample was Stored in formalin for 24 hours then in 700 ethanol at 4° C. for hematoxylin/eosin, Sirius Red Staining.

A NAFLD scoring system (NAS) adapted from Kleiner et al. (*Hepatology*. 41(6):1313-1321 (2005)) was used. An individual mouse NAS total score was calculated for each animal by summing up the score for (1) hepatocellular steatosis, (2) liver inflammation, (3) lobular fibrosis, and (4) hepatocyte ballooning. The spare liver was kept stored at −80° C. for eventual additional analysis.

Data are expressed as mean±SEM. Statistical analysis was performed using a Mann-Whitney test or a 2-way ANOVA+Bonferroni post-test to compare both groups. A p<0.05 was considered significant.

According to another NASH model in mice (See Hsiao et al., *BMC Mol. Biol.* 2008, Sep. 26; 9:92), male C57BL/6 inbred mice, aged 8 weeks, are obtained from BioLASCO Technology (Charles River Taiwan Ltd). All mice receive standard animal care under the supervision of our Institutional Animal Care and Use Committee. The mice are caged in an air-conditioned animal facility at 23° C. on a 12-h light:dark cycle and are maintained with free access to water and food. All the mice are fed with standard chow diet (Basal Diet™ 5755, PMI Nutrition International, St. Louis, MO, USA) for one week. The composition of this basal chow diet is 60.6% (wt/wt) carbohydrate (starch 43.6% and sucrose 16.9%), 10% fat, 19% protein, 4.3% fiber, 5% mineral mixture, and 0.2% vitamin mixture. They are then divided into three groups: (1) chow diet (n=5); (2) high-fat diet (30%) (n=5) (catalog #7166, PMI Nutrition International, Saint Louis, MO, USA); (3) high-fat diet with MIN-102 (3 doses). The high-fat diet, based on basal diet 5755 (contained 40.6% carbohydrate (dextrin 23.6% and sucrose 15%), 15% corn oil, 15% lard, 19% protein, 4.3% fiber, 5% mineral mixture and 0.2% vitamin mixture) provided 53.1% of calories from corn oil and lard.

In another NASH model in mice (See Kus et al., *PLoS ONE* 6(11): e27126 (2011)), male C57BL/6N mice (Charles River Laboratories, Sulzfeld, Germany) are maintained at 22° C. on 12-h light-dark cycle (light from 6:00 AM) with free access to water and Chow (lipid content, 3.4% wt/wt; extruded Ssniff R/M-H diet; Ssniff Spezialdieten GmbH, Soest, Germany). Except for the evaluation of insulin sensitivity in dietary obese, three-month-old mice are randomly assigned (n=8; 2 animals per cage) to cHF diet (lipid content, 35% wt/wt, mainly corn oil; or to the following 'treatments' by (i) cHF+MIN-102 (1 dose); cHF+MIN-102 (3 doses); and cHF+MIN-102 (3 doses). During the treatment lasting for 8, fresh ration of food are distributed daily and food consumption and body weights are recorded once a week. To analyze all the animals under identical nutritional conditions, mice are fasted during the day (between 8:00 AM and 6:00 PM), and then allowed free access to Chow during the night and in the morning until the time of killing the animals under pentobarbital anaesthesia (between 9:00 AM and 11:00 AM). Liver and gastrocnemius muscle are dissected and EDTA-plasma is isolated and stored for further analyses. To characterize the effect of the treatment on insulin sensitivity in obese mice, a separate experiment is performed, in which all the animals are fed cHF diet between 3 and 7 months of age, and then singly caged animals are randomly assigned (n=8) to cHF diet, or they are treated by cHF+MIN-102 doses diet for 2 weeks, i.e., the time when insulin tolerance test is performed. The animal experiments are specifically approved by the Animal Care and Use Committee of the Institute of Physiology Academy of Sciences of the Czech Republic v.v.i. (Approval Number: 172/2009) and conducted under the guidelines.

The insulin tolerance test is performed in overnight fasted mice (food is removed between 5:30 PM and 8:30 AM, i.e., the time of the start of the test by the injection of D-glucose (1 g/kg body weight), in which glycaemia is assessed using tail bleeds just before the injection (fasting blood glucose at the baseline), and during 180 min after the injection using glucometers (LifeScan, USA). Insulin levels are also determined at the baseline and 30 min after the glucose injection. HOMA index was calculated by the following formula: FASTED plasma insulin (mU/l)×FASTED plasma glucose (mmol/l)/22.5. Insulin tolerance test is performed in mice starved for 4 hours (food is removed between 7 AM and 11 AM). At 0, 15, 30 and 90 min following i.p. injection of insulin (0.75 U/kg; Actrapid, Novo Nordisk, Denmark), glucose levels in tail blood are monitored.

As shown in Example 3, the anti-inflammatory potential of MIN-102 was studied in a lipopolysaccharide-induced ("LPS") inflammation model. The human monocytic leukemia cell line THP-1 is chosen for this study because it is a highly differentiated monocytic cell line with phagocytic properties. THP-1 cells can produce pro-inflammatory cytokines (IL-1, IL-6, IL-8, and TNF) and chemokines (MCP-1) in response to lipopolysaccharide ("LPS") (O26:B6, Sigma) stimulation.

In the LPS inflammation test, the cells are grown in 162 cm² flasks in RPMI supplemented with fetal bovine serum at a maximum concentration of $0.8 \times 10^6$ cells/mL. Cells in exponential growth are plated in 24-well tissue culture plates ($0.8 \times 10^6$ cells/well) in serum-free medium at 37° C. in 5% $CO_2$ and pre-incubated with increasing doses of MIN-102 (from 1 μM to 100 μM) for 1 h. After that, 50 ng/mL of LPS is added and incubated for 4 hours. The time, the readout, and the LPS concentration are selected based on previous publications (Singh et al., *Clinical Chemistry* 51(12):2252-2256 (2005)). The supernatants are harvested after 4 hours and stored frozen at −20° C. until analysis. TNF-alpha is quantified in all supernatants by ELISA (Human TNF alpha ELISA Ready-SET-Go, eBioscience).

As shown in FIG. 1, LPS induced the secretion of TNF alpha when compared to the Control group. MIN-102 inhibited the secretion of this cytokine at the highest tested concentrations (100 and 50 μM) and demonstrated minor effects at the lowest tested concentrations (10, 5, and 1 μM). Accordingly, MIN-102 displays anti-inflammatory effects.

Figure 2:
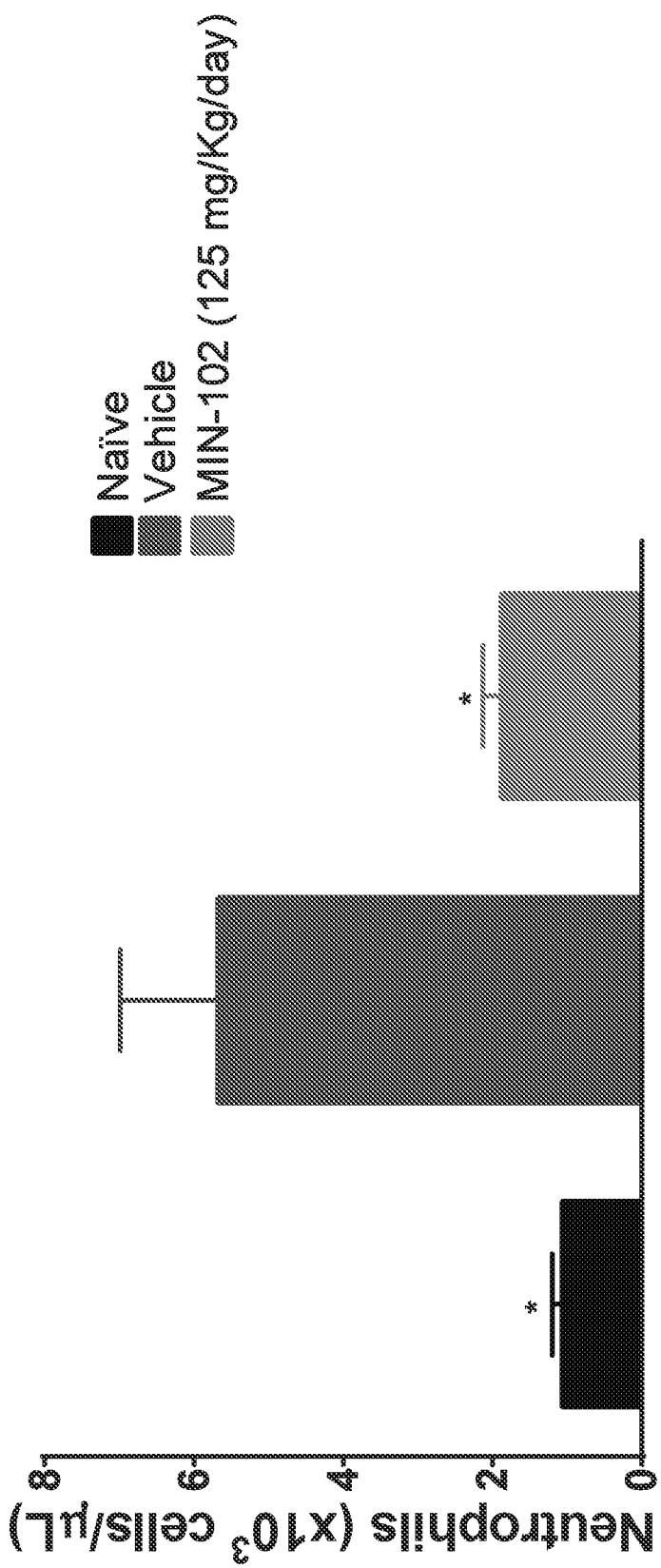
FIG. 2 represents a comparison of the level of neutrophils in an experimental autoimmune encephalitis mouse model after treatment with MIN-102.

As shown in Example 4, the anti-inflammatory potential of MIN-102 was studied using an experimental autoimmune encephalitis ("EAE") mouse model. This model for neuroinflammation is a highly reproducible and long established model of multiple sclerosis. The model is based on the induction of an autoimmune reaction upon the exposure of the animals to myelin antigens. Several days after inoculation, e.g., 9-12 days, the mouse develops a relapsing-remitting or chronic disease course. As shown in FIG. 2, induction of the EAE symptoms increased neutrophils levels, but treatment with MIN-102 reduced the neutrophil levels to values similar to the naïve group. As shown in Table 2, the neutrophil-to-lymphocyte ratio ("NLR") increased in the EAE model and decreased upon MIN-102 treatment. Because the NLR increases in both the EAE model and in NASH patients, it can be concluded based on the data that the NLR for NASH patients can be reduced upon treatment with MIN-102.

Adiponectin is a cytokine that antagonizes excess lipid storage in the liver and protects from inflammation and fibrosis (See, e.g., Buechler et al., *World J. Gastroenterol.* 17(23):2801-2811 (2011)). In patients with NASH, hepatic adiponectin receptors are diminished (See e.g., Kaser et al., *Gut* 54(1):117-121 (2005)). In addition, adiponectin knock-out mice develop a more extensive liver fibrosis compared with wild-type animals, whereas adenovirus-mediated over-expression of adiponectin ameliorates liver damage in wild-type mice (See, e.g., Kamada et al., *Gastroenterology* 125 (6):1796-1807 (2003)). As shown in Example 5 and FIG. 3, treatment with MIN-102 significantly increased the levels of adiponectin. Accordingly, it can be concluded from the data that because the treatment with MIN-102 significantly increases the levels of adiponectin, MIN-102 could also correct the deficiency of adiponectin observed in NASH patients.

Figure 4:
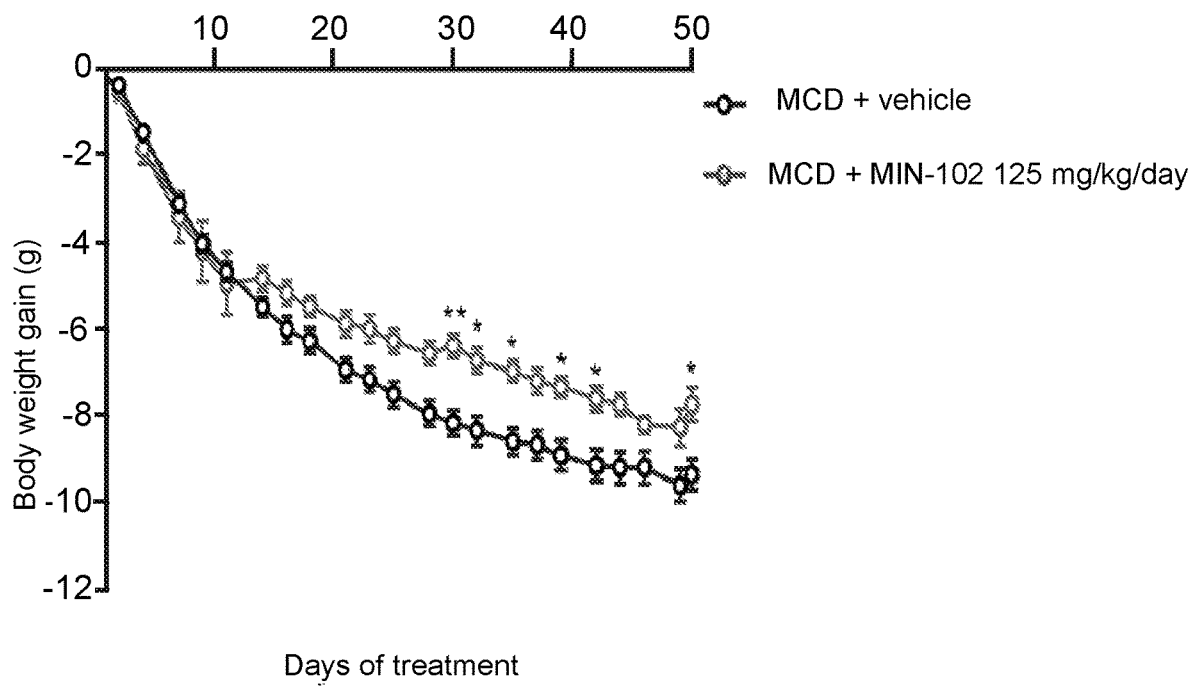
FIG. 4 represents a comparison of the body weight loss in MCD diet NASH mouse model after treatment with MIN-102.
Figure 5A:
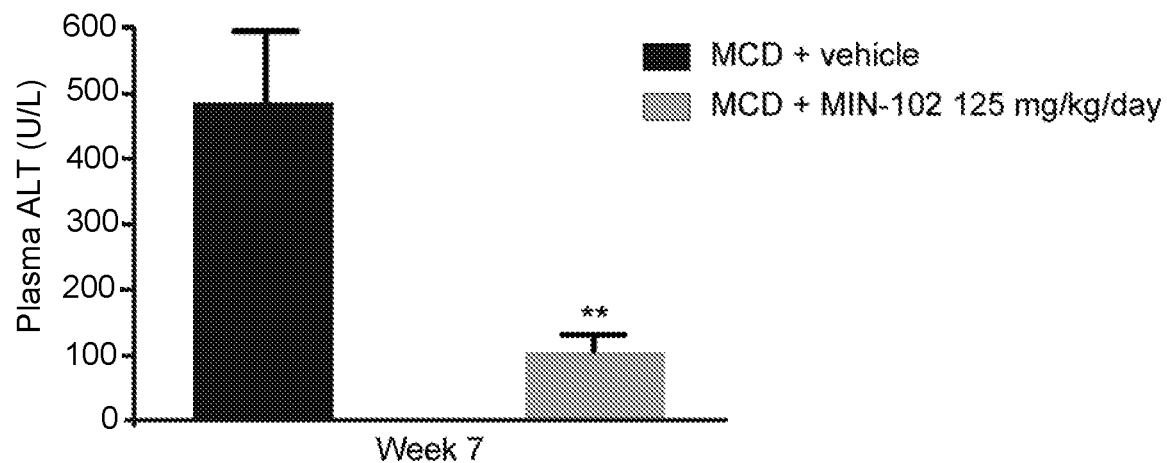
FIG. 5A represents a comparison of plasma ALT levels in MCD diet NASH mouse model after treatment with MIN-102.
Figure 5B:
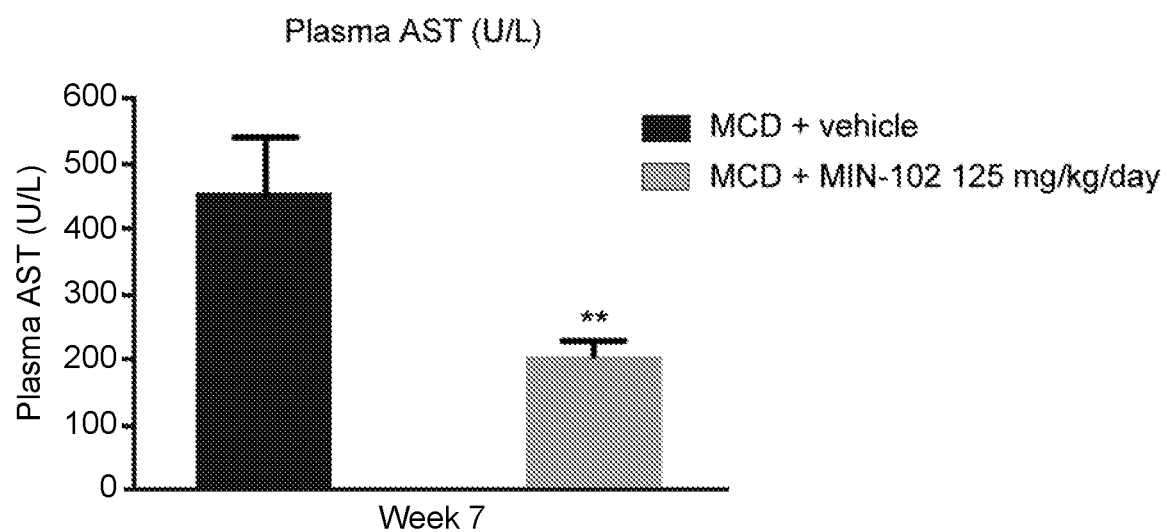
FIG. 5B represents a comparison of plasma AST levels in MCD diet NASH mouse model after treatment with MIN-102.
Figure 6A:
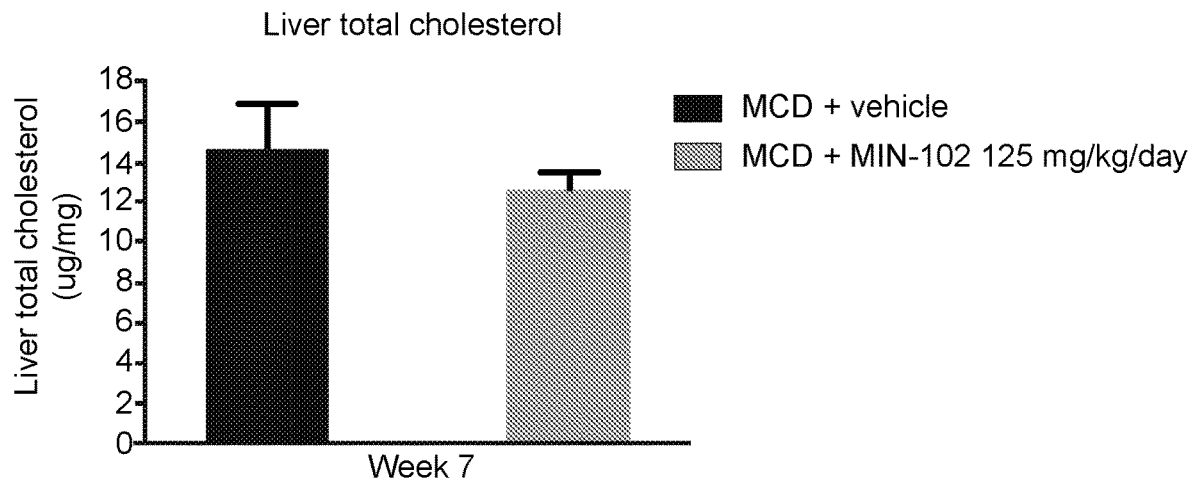
FIG. 6A represents a comparison of liver total cholesterol levels in MCD diet NASH mouse model after treatment with MIN-102.
Figure 6B:
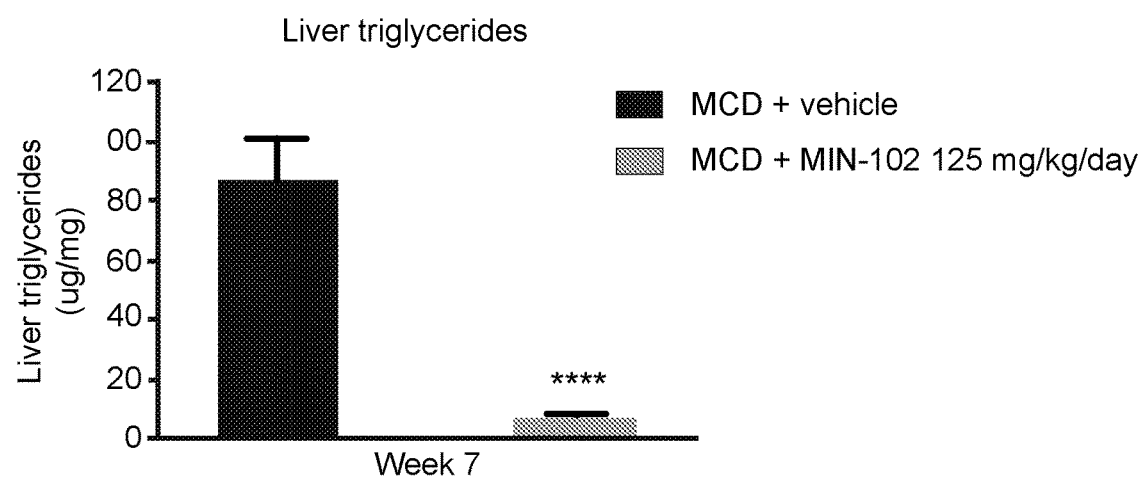
FIG. 6B represents a comparison of the liver triglycerides levels in MCD diet NASH mouse model after treatment with MIN-102.
Figure 7:
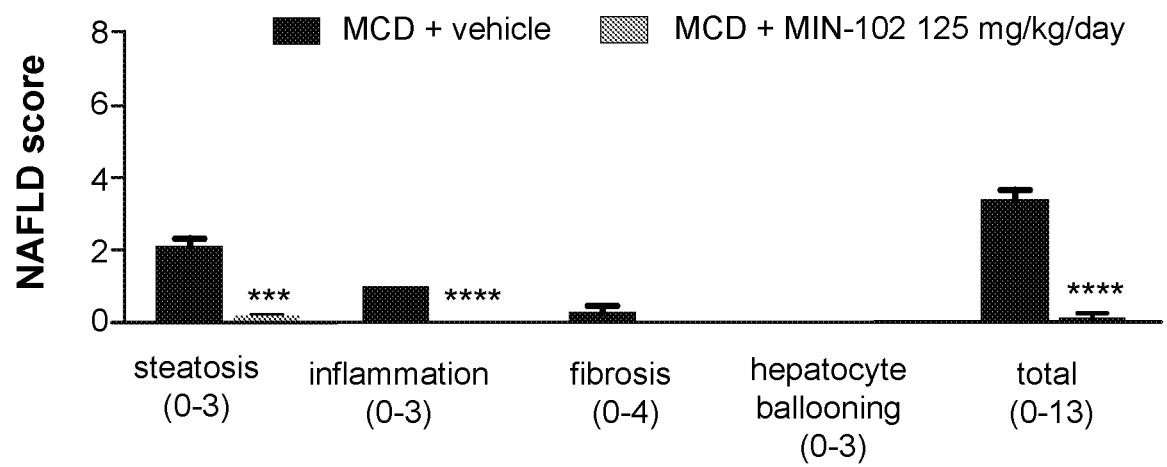
FIG. 7 represents a comparison of the NAFLD score for liver steatosis, inflammation, fibrosis, and hepatocyte ballooning in MCD diet NASH mouse model after treatment with MIN-102.
Figure 8:
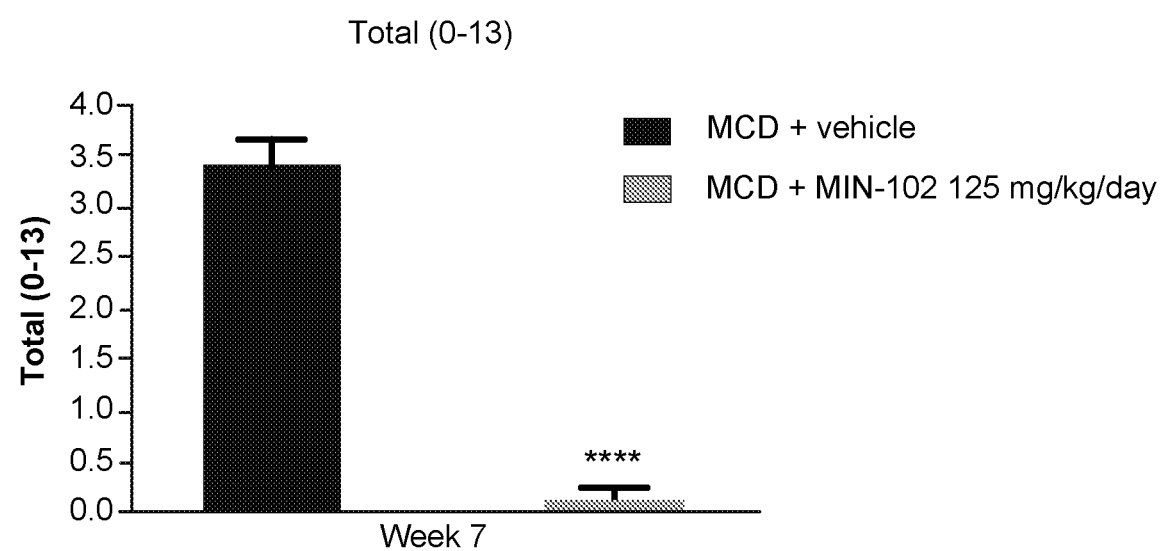
FIG. 8 represents a comparison of the mean NAS scores in MCD diet NASH mouse model after treatment with MIN-102.

As shown in Example 6, the preventative effect of MIN-102 was evaluated in a methionine choline deficient (MCD) diet NASH mouse model. The results of this study demonstrate a strong reduction in liver steatosis and inflammation in MCD mice treated with MIN-102. As shown in FIG. 4, mice treated with MIN-102 showed a less severe decline in body weight loss. FIGS. 5A and 5B show that treatment with MIN-102 substantially reduced both plasma ALT and ALS levels. FIGS. 6A and 6B show that MIN-102 did not change hepatic cholesterol levels, but showed a dramatic reduction in hepatic triglycerides. FIGS. 7 and 8 show a strong reduction in the NAFLD score and NAS score, respectively, for mice treated with MIN-102.

As discussed in Example 7, in humans MIN-102 has less variability in exposure than pioglitazone and, therefore, less risks for the patients are involved with treatment with MIN-102.

Based on their anti-inflammatory activity, Compounds of the Disclosure can also be useful for treating or preventing of a disease selected from the group consisting of skin diseases, inflammation and auto-immune diseases, and inflammatory respiratory diseases. See, e.g., Ellis et al., *Arch. Dermatol.* 136:609-616 (2000); Pershadsingh, *Expert Opin. Investig. Drugs* 13(3):215-228 (2004); and Belvisi et al., *European Journal of Pharmacology* 533:101-109 (2006).

Compounds of the Disclosure have activity as PPAR-γ agonists. PPAR-γ agonists have been reported to be useful in the treatment and/or prevention of a disease selected from the group consisting of chronic granulomatous disorder, a polycystic ovary syndrome, a thyroid carcinoma, a thyroid autoimmune disorder, a pituitary adenoma, atherosclerosis, and hypertension. See, e.g., Migliavacca et al., *J. Allergy Clin. Immunol.* 137:1913-1915 (2016); Du et al., *Adv. Ther.* 29(9):763-774 (2012); Martelli et al., *J. Clin. Endocrinol. Metab.* 87(10):4728-4735 (2002); Grommes et al., *The Lancet Oncology* 5:419-429 (2004); Heaney et al., *J. Clin. Invest.* 111(9):1381-1388 (2003); Hsueh et al., *Arterioscler. Thromb. Vasc. Biol.* 21:1891-1895 (2001); Yamashita et al., *Metabolism* 51(4):403-408 (2002); and Ferrari et al., *PPAR Research* 2015:1-8 (2015).

Pharmaceutical Compositions and Use as a Medicament

Pharmaceutical compositions comprising a Compound of the Disclosure can be administered by any suitable route of administration. For example, any of oral, intraoral, topical, epicutaneous, subcutaneous, transdermal, intramuscular, parenteral, ocular, rectal, vaginal, inhalation, buccal, sublingual and intranasal delivery routes can be suitable. The present disclosure also relates to the use of a compound of formula (1), or a pharmaceutically acceptable salt thereof, in the manufacture of a medicament for the treatment or prevention of NAFLD. In one embodiment, NAFLD is NASH. In another embodiment, the present disclosure relates to the use of a compound of formula (1), or a pharmaceutically acceptable salt thereof, in the manufacture of a medicament for the treatment or prevention of a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

In one embodiment, Compounds of the Disclosure can be administered orally. Oral forms of pharmaceutical compositions can be solid or liquid. Suitable oral dosage forms include tablets, capsules, pills, granules, suspensions, emulsions, syrups or solutions. The pharmaceutical compositions may be a solid form selected from, e.g., tablets, capsules, pills, or granules. In an embodiment, the oral form is a tablet. In another embodiment, the oral form is an oral solution or suspension. These are advantageous when the patient has difficulty swallowing, for example as a result of the disease or for geriatric and pediatric use. Sublingual preparations are also advantageous.

The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Thus, the dose of the active agent will depend on the nature and degree of the condition, the age and condition of the patient, and other factors known to those skilled in the art. A typical daily dosage is from 0.1 to 200 mg, such as from 20 to 200 mg, e.g., for an adult 10-100 mg given as a single dose with no further dosing or in multiple doses, for example one to three times per day. The compounds described herein may also be administered in daily doses of from 80 to 600 mg.

The pharmaceutical compositions may contain conventional excipients known in the art and may be prepared by conventional methods. A specific compound or mixture of compounds may be selected for a particular route of delivery. Some compounds or mixtures of compounds may also be suitable based on their use to treat NAFLD and NASH.

Oral dosage forms may be prepared by combining one or more Compounds of the Disclosure in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, stabilizers, and disintegrating agents.

Due to their ease of administration, tablets, caplets, and capsules (such as hard gelatin, HPMC, or starch capsules) represent an embodiment of the solid oral dosage unit forms, in which case solid pharmaceutical excipients are used. If desired, tablets or caplets can be coated by standard aqueous or nonaqueous techniques. These dosage forms can be prepared by any of the methods of pharmacy. In general, pharmaceutical compositions and dosage forms are prepared by uniformly and intimately admixing one or more Compounds of the Disclosure with liquid carriers, finely divided solid carriers, or both, and then shaping the product into the desired presentation if necessary.

For example, a tablet can be prepared by compression or molding. Compressed tablets can be prepared by compressing in a suitable machine one or more Compounds of the Disclosure in a free-flowing form, such as a powder or granules, optionally mixed with one or more excipients. Molded tablets can be made by molding in a suitable machine a mixture of the powdered compound moistened with an inert liquid diluent.

The pharmaceutical compositions may further comprise one or more other therapeutic agents. Combination treatments may be administered simultaneously, sequentially, or separately, by the same or by different routes, or before, during, and after surgical or intervention procedures.

Compounds of the Disclosure can be used according to the disclosure when the patient is also administered or in combination with one or more of another therapeutic agent selected from antiinflammatory and analgesic agents, antidiabetics (e.g., metformin), dopamine agonists (e.g. levodopa), MAO-B inhibitors, catechol O-methyltransferase (COMT) inhibitors, anticholinergics, other antiparkinsonians (e.g. amantadine), antiNMDA receptors (e.g. memantine), cholinesterase inhibitors, ACE inhibitors, glutamate antagonist (e.g. riluzole), antioxidants, immunomodulators (e.g. fingolimod, anti CD52, CD25 and CD20 monoclonal antibodies, interferon-3-la, natalizumab, laquinimod, dimethylfumarate) chemotherapeutics, enzyme replacement therapy agents, substrate reduction therapy agents, corticosteroids, antiproliferatives (e.g. methotrexate), anticonvulsant medications, anticoagulants, antihypertensives and neuroprotectives. The compounds of the disclosure may also be used when the patient is undergoing gene therapy, bone marrow transplantation, deep brain stimulation or radiotherapy.

The one or more therapeutic agents include a sulfonylurea (e.g., glimepiride, glipizide, glyburide), a glinidine (also known as meglitinides), a thiazolidinedione (e.g., pioglitazone, rosiglitazone, lobeglitazone), a dipeptidyl peptidase 4 (DPP4) inhibitor (e.g., sitagliptin, vildagliptin, saxagliptin, linagliptin, gemigliptin, anagliptin, teneligliptin, alogliptin, trelagliptin, dutogliptin, omarigliptin), a sodium/glucose cotransporter 2 (SGLT2) inhibitor (e.g., canagliflozin, dapagliflozin), a glucagon-like peptide-1 (GLP1) receptor agonist (e.g., exenatide, liraglutide, lixisenatide, albiglutide, dulaglutide, taspoglutide, semaglutide), glucagon like peptide-1 (GLP-1), and insulin (e.g., animal insulin preparations extracted from the pancreas of cattle or pigs; human insulin preparations synthesized by genetic engineering using *Escherichia coli* or yeast; insulin zinc; protamine insulin zinc; insulin fragments or derivatives (e.g., INS-1), and oral insulin preparations.

EXAMPLES

The methods of treatment or prevention and uses described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1

Evaluation of Bladder Epithelium Hyperplasia in Rat Tissue

Tissue samples from treated rats either with pioglitazone (two doses 14.5 and 145 mg/Kg/day) or MIN-102 (25, 100, and 150 mg/Kg/day) were routinely processed, fixed in 10% buffered formalin, embedded in paraffin, and stained with hematoxylin and eosin.

Tissue bladder urothelium sections from rats treated with MIN-102, pioglitazone, or placebo was observed for hyperplasia, cytotoxicity, and necrosis with light microscopy by an expert pathologist and classified as non, slight, mild, and severe hyperplasia.

Epithelium hyperplasia, which is a predictive marker of a possible risk of bladder cancer, was only observed in the pioglitazone group (See Suzuki et al., *Toxicological Sciences* 113(2):349-357 (2010)).

Example 2

CYP Inhibition and Induction of MIN-102

As shown in Table 1, reversible and time-dependent inhibition (TDI) of MIN-102 towards major drug metabolizing cytochrome P450 (CYP) enzymes was investigated to evaluate potential drug-drug interactions of MIN-102.

Inhibition was screened using a cocktail incubation with CYP specific substrates for eight major drug metabolizing CYP enzymes (CYPs 1A2, 2A6, 2B6, 2C8, 2C9, 2C19, 2D6 and 3A4) in incubations with a pool of human liver microsomes. In reversible inhibition, MIN-102 was incubated with buffer, microsomes, cofactor NADPH and CYP-specific substrate cocktail mix for 15 min. In TDI study, buffer and microsomes were preincubated with MIN-102 in the presence and absence of cofactor NADPH for 0 or 30 min to elucidate the possible time-dependency of inhibition. Secondary incubation was conducted with CYP-specific substrate cocktail mix for 30 min. MIN-102 was used at final concentrations of 0.01, 0.1, 1, 10, and 100 µM in both assays.

TABLE 1

CYP inhibition:

| Enzyme | Reaction | IC$_{50}$ (µM) | Tentative K$_i$ (µM) |
|---|---|---|---|
| CYP1A2 | ACET | >>100 | — |
| CYP2A6 | 7OH-COU | >>100 | — |
| CYP2B6 | OH-BUP | >>100 | — |
| CYP2C8 | OH-REPA | 102* | 84 |
| CYP2C9 | OH-DICL | 103* | 52 |
| CYP2C19 | 5-OH-OME | >>100 | — |
|  | dem-OME | >>100 | — |
| CYP2D6 | O-dem-DEX | >>100 | — |
| CYP3A4 | 1-OH-MDZ | >>100 | — |
|  | 6β-OH-TES | >>100 | — |
|  | 3-OH-OME | >>100 | — |
|  | SO-OME | >>100 | — |

MIN-102 did not cause remarkable reversible or time-dependent inhibition towards major CYP enzymes at in vitro concentrations of 100 µM or lower.

These data differed from those of pioglitazone. Pioglitazone (see tables from Sahi et al., *Drug Metabolism and Disposition* 31(4):439-446 (2003)) exhibits an IC$_{50}$ for 2C8 of 9.38 µM with a K$_i$ of 1.69 µM; and for 3A4 of 12.3 µM and with a K$_i$ of 11.8.

Pioglitazone appears to be an inhibitor of these CYPs as well as being metabolized extensively by CYP2C8 to MIN-102. However, MIN-102 does not exhibit potent inhibition of CYP2C8 or CYP3A4.

The data generated did not indicate MIN-102 as a strong inducer of CYP1A2, CYP21B6, or CYP3A4 at the concentrations tested. However, minor induction signal at the highest tested MIN4-102 concentration (50 µM) suggested that induction at higher concentrations cannot be ruled out. MIN4-102 is cleaner than pioglitazone as a potential CYP inducer.

The induction potency of MIN-102 at five concentrations ranging from 0.1 to 50 µM towards human CYP enzymes 1A2, 2B36, and 3A4 at mRNA and enzyme activity level was studied in cryopreserved hepatocytes from 3 human donors. The stability of MIN-102 in the incubation medium was assayed in parallel at the highest test concentration (50 µM) and quantified in incubation medium.

Minor, less than 20% of the respective positive control induction, increase in CYP3A4 mRNA and activity of CYP1A2, CYP2B6, and CYP3A4 probe reactions was observed at the highest MIN-102 concentration (50 µM). Thus, the data generated do not indicate MIN-102 is a strong inducer of CYP1A2, CYP2B6, or CYP3A4 at the concentrations tested.

Based on stability experiments, MIN-102 at a concentration of 50 µM remained stable during 24-hour incubation, suggesting no evidence that decay of MIN-102 during incubations would have biased the evaluation of induction potential of MIN-102.

In contrast, pioglitazone in a similar assay induced 4.79 fold at 10 µM in CYP3A4 and 2.35 at 50 µM in CYPB6, which are >20% of positive controls induction.

Example 3

MIN-102 Shows Anti-Inflammatory Effects in an In Vitro Lipopolysaccharide-Induced Inflammation Model Human monocytic leukemia THP-1 cells were obtained from the American Type Culture Collection. The cells were maintained in RPMI-1640 medium with 11.1 mmol/L glucose, 0.05 mmol/L mercaptoethanol, 100 mL/L or 10% fetal bovine serum, and 2 mmol/L glutamine.

The human monocytic leukemia cell line THP-1 was chosen for this study because it is a highly differentiated monocytic cell line with phagocytic properties. The THP-1 cell line was used in this in vitro model, rather than human monocytes, to minimize variability.

The cells were grown in 162 cm$^2$ flasks in RPMI supplemented with fetal bovine serum at a maximum concentration of 0.8×10$^6$ cells/mL. Cells in exponential growth were plated in 24-well tissue culture plates (0.8×10$^6$ cells/well) in serum-free medium at 37° C. in 5% CO$_2$ and pre-incubated with increasing doses of MIN-102 (from 1 µM to 100 µM) for 1 h. After that, 50 ng/mL of LPS was added and incubated for 4 hours. The time, the readout, and the LPS concentration were selected based on previous publications (Singh et al., *Clinical Chemistry* 51(12):2252-2256 (2005)). The supernatants were harvested after 4 hours and stored frozen at −20° C. until analysis. TNF-alpha was quantified in all supernatants by ELISA (Human TNF alpha ELISA Ready-SET-Go, eBioscience). The range of TNF-alpha calibrators was 0-500 ng/L. Data are presented as mean+ standard error of the mean of three replicate wells per treatment. Data was statistically analyzed by one-way ANOVA followed by Bonferroni post-hoc test vs. Control+ LPS treatment (*, p<0.05; ***, p<0.001).

As shown in FIG. 1, LPS induced the secretion of TNF alpha when compared to the Control group. MIN-102 inhibited the secretion of this cytokine at the highest tested concentrations (100 and 50 µM) and demonstrated minor effects at the lowest tested concentrations (10, 5, and 1 µM). Accordingly, MIN-102 displays anti-inflammatory effects.

Example 4

MIN-102 Exhibits Anti-Inflammatory Properties in Experimental Autoimmune Encephalitis ("EAE") Mouse Model The anti-inflammatory potential of MIN-102 was studied using an EAE mouse model, e.g., as described in Linker and Lee, *Experimental & Translational Stroke Medicine* 1:5 (2009). This model for neuroinflammation is a highly reproducible and long established model of multiple sclerosis. The model is based on the induction of an autoimmune reaction upon the exposure of the animals to myelin antigens. Several days after inoculation, e.g., 9-12 days, the mouse develops a relapsing-remitting or chronic disease course.

In the study, female C57Bl/6 mice were sensitized by a subcutaneous injection of myelin oligodendrocyte glycoprotein peptide fragment 35-55 (MOG$_{35-55}$) in Freund's Complete Adjuvant (CFA) at the tail base. Starting at five days after disease induction, the animals were treated at three different oral doses of MIN-102, 17, 50, and 125 mg/Kg/day, using bid administration. From day five, the animals were weighed and scored for the appearance of disease symptoms. The levels of neutrophils were measured in mice from the naïve, vehicle, and the highest MIN-102 dose. Data were analyzed by one-way ANOVA followed by the Dunnett's post-hoc test versus the vehicle group (*, p <0.05). Results are presented as mean+standard error of the mean of n=10, except n=9 for the highest dose of MIN-102, and n=4 for the naïve group.

TABLE 2

Neutrophil-to-lymphocyte ratio ("NRL") in EAE

| | Neutrophil number ×10³ cells/μl | Lymphocyte number ×10³ cells/μl | N/L ratio |
|---|---|---|---|
| Naïve | 1.1 ± 0.2 | 4.6 ± 1.1 | 0.24 |
| EAE mice | 5.7 ± 3 | 4.7 ± 1.2 | 1.21 |
| EAE mice + MIN-102 highest dose | 1.9 ± 0.6 | 3.6 ± 2.3 | 0.52 |

As shown in FIG. 2, after induction of the EAE symptoms, the levels of neutrophils increased, but treatment with MIN-102 reduced the numbers to values similar to the naïve group. As shown in Table 2, the neutrophil-to-lymphocyte ratio (NLR) increased in the EAE model and decreased upon MIN-102 treatment.

Because the NLR increases in both the EAE model and in NASH patients (See, e.g., Alkhouri et al., *Liver Int.* 32(2): 297-302 (2012)), it can be concluded based on the data that the NLR for NASH patients can also be reduced upon MIN-102 treatment. Accordingly, it is expected that MIN-102 can effectively treat NASH by reducing NRL.

Example 5

IN-102 Significantly Increases Adiponectin Levels in Plasma

Hepatic adiponectin receptors are diminished in NASH patients and adiponectin knockout mice develop a more extensive liver fibrosis compared with wild-type animals, whereas adenovirus-mediated overexpression of adiponectin ameliorates liver damage in wild-type mice. (See, e.g., Kamada et al., *Gastroenterology* 125:1796-1807 (2003)).

The PPAR engagement in the central nervous system was performed in Sprague Dawley wild type rats. The rats were treated for 7 days with increasing doses of MIN-102 at 54 mg/Kg/day. Plasma were obtained at 1 h after the last MIN-102 administration. Adiponectin levels were measured by ELISA. Results were represented as mean+standard error of the mean of n=8. Data were analyzed by Kruskal-Wallis followed by the Dunn post-hoc test versus the vehicle group (****, p<0.0001).

Figure 3:
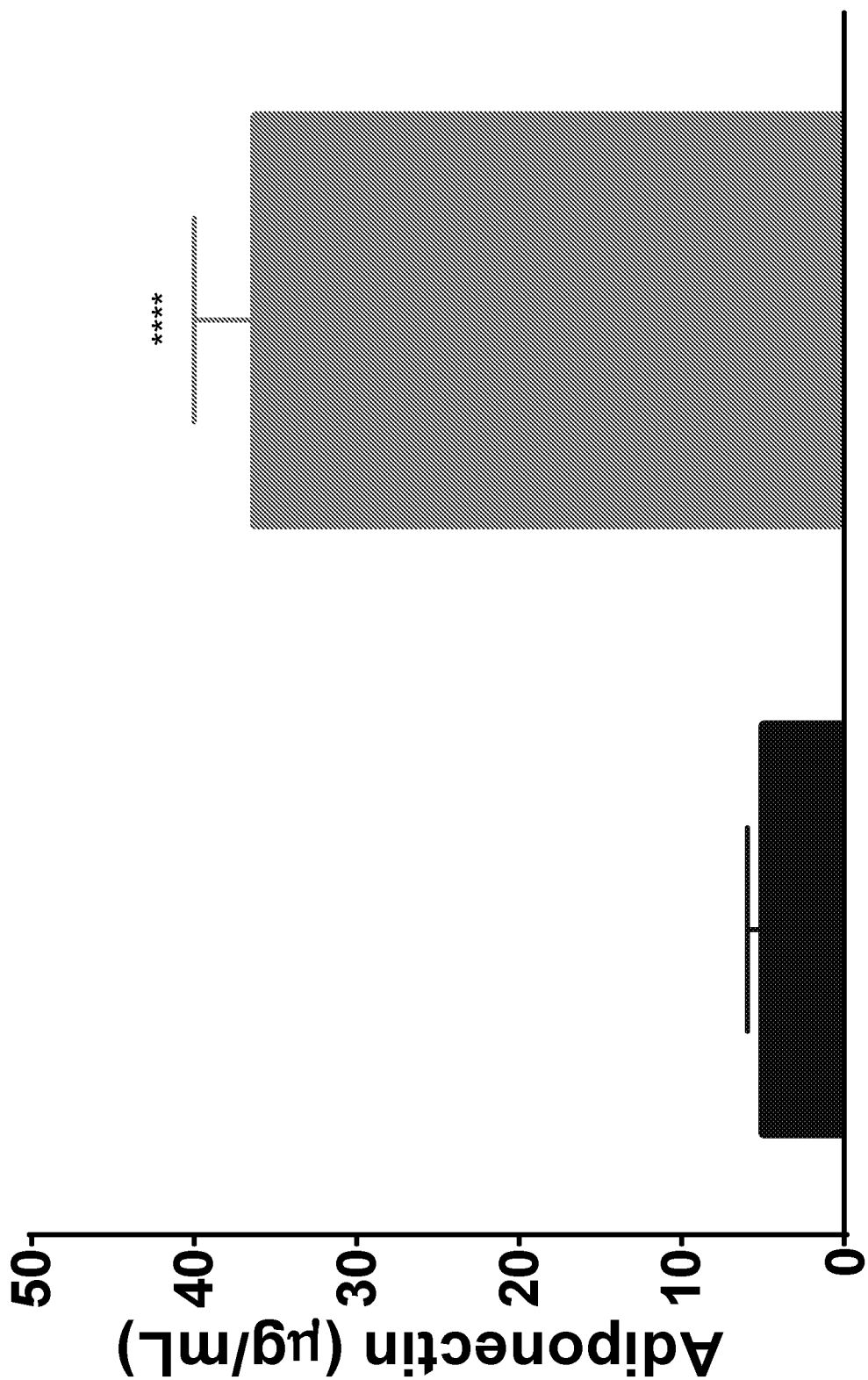
FIG. 3 represents a comparison of adiponectin levels in Sprague Dawley rats after treatment with MIN-102.

As shown in FIG. 3, MIN-102 treatment significantly increased the levels of adiponectin. Accordingly, it can be concluded based on these data that because MIN-102 treatment significantly increases the levels of adiponectin, MIN-102 could also correct the deficiency of adiponectin observed in NASH patients.

Example 6

Effects of MIN-102 in the Methionine Choline Deficient Diet Fed Mice

The preventive effects of MIN-102 was evaluated in a 7-week Methionine Choline Deficient (MCD) diet NASH mouse model (Verdelho Machado et al.). After the acclimation period, C57BL6/J male mice (n=20) were weighed and randomized into 2 homogenous treatment groups based on body weight (n=10/group), put on a MCD diet, and treated BID orally with vehicle or MIN-102 for 7 weeks.

MIN-102 was dosed 62.5 mg/kg BID orally by gavage.

When C57BL6/J mice are fed a MCD diet, they rapidly develop liver steatosis, inflammation and fibrosis with concomitant increase in plasma alanine transaminase (ALT)/ aspartate aminotransferase (AST) levels.

Material and Methods

After the acclimation period, C57BL6/J male mice (n=20) were weighed and randomized into 2 homogenous treatment groups based on body weight (n=10/group), put on a MCD diet, and treated BID orally with a vehicle or MIN-102 (125 mg/Kg/day) for 7 weeks. Body weight was measured 3 times/week until the end of the experimental phase.

At 7 weeks of diet/treatment, mice were weighed and treated at ~08:00 am in the morning, then bled (maximal volume/EDTA) at ~1:00 pm. Plasma was then immediately isolated and stored at −80° C. prior to assay plasma ALT and AST. The plasma volume left over was stored at −80° C. for eventual additional analysis.

After blood collection, the mice were sacrificed by cervical dislocation under isoflurane anesthesia and exsanguinated with sterile saline.

A NAFLD scoring system (NAS) adapted from Kleiner et al. (*Hepatology*. 41(6):1313-1321 (2005)) using the criteria described in the Table 3 below:

TABLE 3

NAFLD Scoring System ("NAS")

| Score | Steatosis | Inflammation | Fibrosis | Hepatocyte ballooning |
|---|---|---|---|---|
| 0 | <5% of liver parenchyma | No foci | None | None |
| 1 | 5-to-33% of liver parenchyma | <2 foci at 20x field | Zone 3 and/or perisinusoidal fibrosis | Minimal to mild focal involving fewer than 3 hepatocytes per foci |
| 2 | 34-to-66% of liver parenchyma | 2-to-4 foci at 20x field | As grade 1 and portal fibrosis | Moderate multifocal involving more than 3 hepatocytes per foci |

TABLE 3-continued

NAFLD Scoring System ("NAS")

| Score | Steatosis | Inflammation | Fibrosis | Hepatocyte ballooning |
|---|---|---|---|---|
| 3 | >66% of liver parenchyma | >4 foci at 20x field | As grade 2 and bridging fibrosis | Prominent multifocal involving large number of hepatocytes |
| 4 | Not applicable | Not applicable | Cirrhosis | Not applicable |

Several other histopathological observations described in clinical human cases and originally reported in the NAS scoring system published by Kleiner et al. were not observed in this animal study, such as lipogranuloma, acidophil bodies, megamitochondria, and pigmented macrophages. Therefore, it was elected not to include them in the scoring system described above. An individual mouse NAS total score was calculated for each animal by summing up the score for (1) hepatocellular steatosis, (2) liver inflammation, (3) lobular fibrosis, and (4) hepatocyte ballooning.

Results

As expected, the mice under MCD diet showed substantial body weight loss. However, as shown in FIG. 4, the mice treated with MIN-102 showed a less severe decline in body weight loss, from day 14 to day 50, leading to significant differences between day 30 and day 50.

As also expected, MCD diet resulted in very high ALT and AST plasma levels (mean values of 480 U/L and 455 U/L, respectively) at the end of the treatment. FIGS. 5A and 5B show that treatment with MIN-102 substantially reduced both plasma ALT and AST levels by 78% and 55%, respectively (both p<0.01 vs. vehicle).

As shown in FIGS. 6A and 6B, the mice treated with MIN-102 did not show a change in hepatic cholesterol levels, but showed a dramatic reduction in hepatic triglycerides levels by 92% (p<0.001 vs. vehicle).

Histology analysis was performed (oil red O, H&E and Sirius Red staining) for NAFLD scoring system (NAS) for liver steatosis, inflammation, fibrosis and hepatocyte ballooning shown in FIG. 7.

Mean NAS group scores were 3.40±0.3 and 0.44±01 in vehicle and MIN-102, respectively (p<0.001 vs. vehicle) (FIG. 8). The strong reduction in the NAS score was related to a blunted steatosis score (p<0.001 vs. vehicle), which was confirmed by an extremely low oil red o staining % as compared with vehicle (p<0.001), and a total disappearance of inflammation.

In conclusion, the present study demonstrates a strong reduction in liver steatosis and inflammation in MCD mice treated with MIN-102.

Example 7

Comparison of the Variability (CV %) in Pharmacokinetic AUC (Area Under Curve, Exposure) ng·hr/ml Data Between Pioglitazone and MIN-102 Treatment in Healthy Volunteers According to a recent publication, pioglitazone is a safe and effective option to manage patients with type 2 diabetes and nonalcoholic steatohepatitis (NASH) (Kawaguchi-Suzuki et al., *Aliment. Pharmacol. Ther.* 46(1):56-61 (2017)). However, as stated in this publication, there is marked variability in the treatment response. Kawaguchi-Suzuki et al. describe that the response to pioglitazone in NASH patients was concentration-dependent as evidenced by the significant relationship between both pioglitazone concentration and pioglitazone exposure index with changes in NAS (r=0.48, P=0.0002 and r=0.51, P<0.0001, respectively), steatosis (r=0.41, P=0.002 and r=0.46, P=0.0005), and inflammation (r=0.44, P=0.0009 and r=0.40, P=0.0003).

The pioglitazone exposure index was also associated with a change in ballooning (P=0.04). The pioglitazone exposure index was higher in patients with NASH resolution (2.85_1.38 vs 1.78_1.48, P=0.018). A predictive model for the primary outcome was developed by the authors that incorporated baseline NAS and pioglitazone exposure index (AUC (area under curve)=0.77). Due to its PK variability, pioglitazone was not effective in all NASH patients, and higher doses would be required to ensure its efficacy in all treated NASH patients. Higher doses of pioglitazone would increase the risk of developing adverse events.

Eckland et al. and Christensen et al. report that the variability (CV %; coefficient of variation) in pioglitazone clearance is typically about 40%-50% (Table 4), yielding a range in exposure (AUC) that is up to 10-fold (Eckland et al., *Exp. Clin. Endocrinol. Diabetes* 108 (Suppl. 2):5234-5242 (2000); Christensen et al., *J. Clin. Pharmacol.* 45:1137-1144 (2005)).

TABLE 4

Pioglitazone data from 3 studies (a, b, c) in healthy subjects and evaluated a single oral dose 45 mg provided as mean ± SD

| | $AUC_{0-\infty}$ (ng · h/ml) | | |
|---|---|---|---|
| Study | mean | SD (standard deviation) | CV % |
| a | 13854 | 4996 | 35 |
| b | 14458 | 7434 | 51 |
| c | 14071 | 5727 | 40 |

In contrast, the variability after MIN-102 administration in comparable conditions in healthy volunteers shows much less variability with a CV % between 10-20% (Table 5). Thus, MIN-102 treatment could be more predictable in reaching effective doses needing less adjustments than a pioglitazone treatment and consequently would involve less risks in safety potential issues due to high doses.

TABLE 5

CV % of MIN-102 from a study (SAD) in healthy subjects and evaluated at single oral doses of 30, 90, and 270 mg

| Dose MIN-102 mg | CV % |
|---|---|
| 30 | 9.00 |
| 90 | 9.00 |
| 270 | 18.00 |

After MIN-102 administration, the $AUC_{0-\infty}$ value at the various doses of MIN-102 tested is substantially higher than when administering a comparable dose of pioglitazone.

Some doses can provide an $AUC_{0-\infty}$ within the range of about 20,000-400,000 ng·h/ml.

The disclosure also relates to:

[1] A method of treating or preventing nonalcoholic fatty liver disease, comprising administering to a subject in need thereof a compound of formula (1)

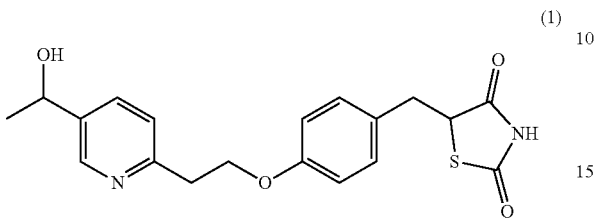
(1)

or a pharmaceutically acceptable salt thereof, in an amount effective to treat or prevent nonalcoholic fatty liver disease.

[2] The method according to [1], wherein the nonalcoholic fatty liver disease is nonalcoholic steatohepatitis.

[3] A method of treating or preventing a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease, comprising administering to a subject in need thereof a compound of formula (1)

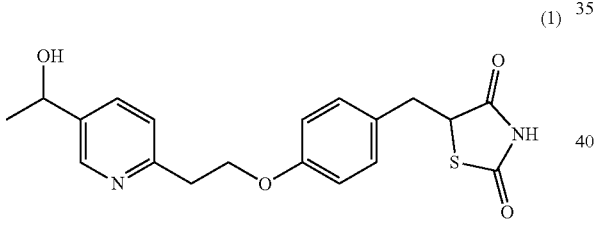
(1)

or a pharmaceutically acceptable salt thereof, in an amount effective to treat or prevent a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

[4] The method according to any one of [1] to [3], wherein the compound of formula (1) is selected from the group consisting of:

(2)  (R)-5-[[4-[2-[5-(R)-(1-hydroxyethyl)pyridin-2-yl]ethoxy]phenyl]methyl]-1,3-thiazolidine-2,4-dione;
(3)  (R)-5-[[4-[2-[5-(S)-(1-hydroxyethyl)pyridin-2-yl]ethoxy]phenyl]methyl]-1,3-thiazolidine-2,4-dione;
(4)  (S)-5-[[4-[2-[5-(R)-(1-hydroxyethyl)pyridin-2-yl]ethoxy]phenyl]methyl]-1,3-thiazolidine-2,4-dione; or
(5)  (S)-5-[[4-[2-[5-(S)-(1-hydroxyethyl)pyridin-2-yl]ethoxy]phenyl]methyl]-1,3-thiazolidine-2,4-dione;
or a pharmaceutically acceptable salt thereof.

[5] The method according to [4], comprising administering a mixture of two or more of compounds selected from the group consisting of compound (2), compound (3), compound (4), and compound (5), or a pharmaceutically acceptable salt thereof, wherein the mixture is optically active.

[6] The method according to [5], wherein the mixture comprises:
(a) the compound (2) and the compound (3);
(b) the compound (4) and the compound (5);
(c) the compound (2) and the compound (4); and
(d) the compound (3) and the compound (5),
or a pharmaceutically acceptable salt thereof.

[7] The method according to any one of [1] to [6], further comprising administering another therapeutic agent.

[8] The method according to [7] wherein the compound of formula (1), or a pharmaceutically acceptable salt thereof, and said another therapeutic agent are provided in combination.

[9] The method according to any one of [1] to [8], wherein no more than 1% of the total number of hydrogen atoms per mole of the compound of formula (1) are in the form of the $^2H$ isotope.

[10] The method according to any one of [1] to [9], wherein the compound of formula (1), or a pharmaceutically acceptable salt thereof, is administered to the subject in an oral, intraoral, topical, epicutaneous, subcutaneous, transdermal, intramuscular, parenteral, ocular, rectal, vaginal, inhalation, buccal, sublingual, or intranasal dosage form.

[11] The method according to [10], wherein the dosage form is an oral dosage form.

[12] The method according to [11], wherein the oral dosage form is an oral solution or an oral suspension.

[13] A compound of formula (1), or a pharmaceutically acceptable salt thereof, for use in the treatment or prevention of nonalcoholic fatty liver disease

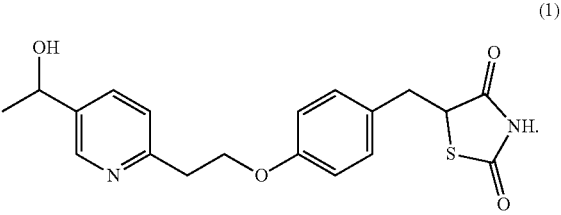 [SMILES: CC(O)c1ccc(CCOc2ccc(CC3SC(=O)NC3=O)cc2)nc1]
(1)

[14] The compound for use according to [13], wherein the nonalcoholic fatty liver disease is nonalcoholic steatohepatitis.

[15] A compound of formula (1), or a pharmaceutically acceptable salt thereof, for use in the treatment or prevention of a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

[16] The compound for use according to any one of [13] to [15], wherein the compound of formula (1) is:
(2)  (R)-5-[[4-[2-[5-(R)-(1-hydroxyethyl)pyridin-2-yl]ethoxy]phenyl]methyl]-1,3-thiazolidine-2,4-dione;
(3)  (R)-5-[[4-[2-[5-(S)-(1-hydroxyethyl)pyridin-2-yl]ethoxy]phenyl]methyl]-1,3-thiazolidine-2,4-dione;
(4)  (S)-5-[[4-[2-[5-(R)-(1-hydroxyethyl)pyridin-2-yl]ethoxy]phenyl]methyl]-1,3-thiazolidine-2,4-dione; and (5) (S)-5-[[4-[2-[5-(S)-(1-hydroxyethyl)pyridin-2-yl]ethoxy]phenyl]methyl]-1,3-thiazolidine-2,4-dione;
or a pharmaceutically acceptable salt thereof.

[17] The compound for use according to any one of [13] to [16], wherein no more than 1% of the total number of hydrogen atoms per mole of the compound of formula (1) are in the form of the $^2$H isotope.

[18] A mixture of two or more of compounds selected from the group consisting of compound (2), compound (3), compound (4), and compound (5) as defined in [13], or a pharmaceutically acceptable salt thereof, for use in the treatment or prevention of nonalcoholic fatty liver disease, wherein the mixture is optically active.

[19] The mixture for use according to [18], wherein said mixture comprises:
(a) the compound (2) and the compound (3);
(b) the compound (4) and the compound (5);
(c) the compound (2) and the compound (4); and
(d) the compound (3) and the compound (5),
or a pharmaceutically acceptable salt thereof.

[20] Use of a compound of formula (1), or a pharmaceutically acceptable salt thereof, in the manufacture of a medicament for the treatment or prevention of nonalcoholic fatty liver disease

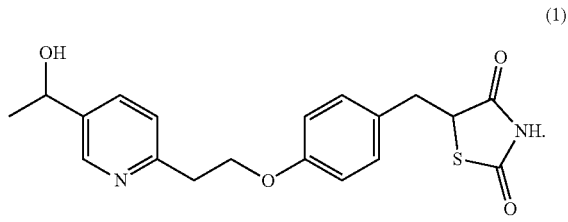 [SMILES: CC(O)c1ccc(CCOc2ccc(CC3SC(=O)NC3=O)cc2)nc1]

(1)

[21] The use according to [20], wherein the nonalcoholic fatty liver disease is nonalcoholic steatohepatitis.

[22] Use of a compound of formula (1), or a pharmaceutically acceptable salt thereof, in the manufacture of a medicament for the treatment or prevention of a disease selected from the group consisting of a chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease

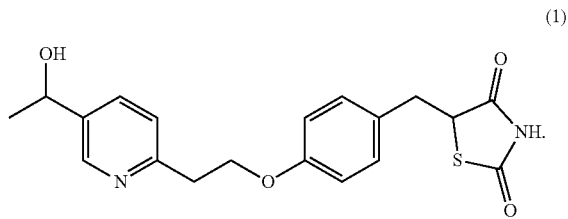

(1)

[23] The use according to any one of [20] to [22], wherein the compound of formula (1) is:
(2) (R)-5-[[4-[2-[5-(R)-(1-hydroxyethyl)pyridin-2-yl]ethoxy]phenyl]methyl]-1,3-thiazolidine-2,4-dione;
(3) (R)-5-[[4-[2-[5-(S)-(1-hydroxyethyl)pyridin-2-yl]ethoxy]phenyl]methyl]-1,3-thiazolidine-2,4-dione;
(4) (S)-5-[[4-[2-[5-(R)-(1-hydroxyethyl)pyridin-2-yl]ethoxy]phenyl]methyl]-1,3-thiazolidine-2,4-dione; or
(5) (S)-5-[[4-[2-[5-(S)-(1-hydroxyethyl)pyridin-2-yl]ethoxy]phenyl]methyl]-1,3-thiazolidine-2,4-dione;
or a pharmaceutically acceptable salt thereof.

[24] The use according to [23], wherein said medicament comprises a mixture of two or more of compounds selected from the group consisting of compound (2), compound (3), compound (4), and compound (5), wherein the mixture is optically active.

[25] The use according to [24], wherein the mixture comprises:
(a) the compound (2) and the compound (3);
(b) the compound (4) and the compound (5);
(c) the compound (2) and the compound (4); and
(d) the compound (3) and the compound (5),
or a pharmaceutically acceptable salt thereof.

Having now fully described this disclosure, it will be understood by those of ordinary skill in the art that the same can be performed within a wide and equivalent range of conditions, formulations, and other parameters without affecting the scope of the invention or any embodiment thereof.

Other embodiments of the disclosure will be apparent to those skilled in the art from consideration of the specification and practice of the invention disclosed herein. It is intended that the specification and examples be considered exemplary only, with a true scope and spirit of the invention being indicated by the following claims.

All patents, patent applications, and publications cited herein are fully incorporated by reference herein in their entirety.

The invention claimed is:

1. A method of treating nonalcoholic fatty liver disease, comprising administering to a subject in need thereof a dosage form comprising an effective amount of a compound of formula (1)

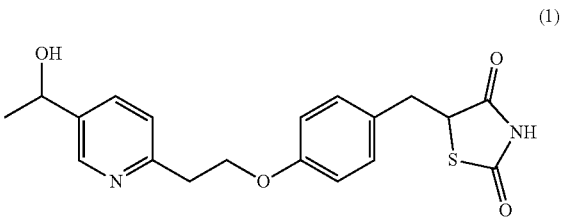 [SMILES: CC(O)c1ccc(CCOc2ccc(CC3SC(=O)NC3=O)cc2)nc1]

(1)

or a pharmaceutically acceptable salt thereof, wherein the nonalcoholic fatty liver disease is nonalcoholic steatohepatitis.

2. The method according to claim 1, wherein the compound of formula (1) is selected from the group consisting of:
(2) (R)-5-[[4-[2-[5-(R)-(1-hydroxyethyl)pyridin-2-yl]ethoxy]phenyl]methyl]-1,3-thiazolidine-2,4-dione;
(3) (R)-5-[[4-[2-[5-(S)-(1-hydroxyethyl)pyridin-2-yl]ethoxy]phenyl]methyl]-1,3-thiazolidine-2,4-dione;
(4) (S)-5-[[4-[2-[5-(R)-(1-hydroxyethyl)pyridin-2-yl]ethoxy]phenyl]methyl]-1,3-thiazolidine-2,4-dione; and
(5) (S)-5-[[4-[2-[5-(S)-(1-hydroxyethyl)pyridin-2-yl]ethoxy]phenyl]methyl]-1,3-thiazolidine-2,4-dione;
or a pharmaceutically acceptable salt thereof.

3. The method according to claim 1, wherein the dosage form comprises a mixture of two or more of compounds of formula (1) selected from the group consisting of compound (2): (R)-5-[[4-[2-[5-(R)-(1-hydroxyethyl)pyridin-2-yl]ethoxy]phenyl]methyl]-1,3-thiazolidine-2,4-dione, compound (3): (R)-5-[[4-[2-[5-(S)-(1-hydroxyethyl)pyridin-2-yl]ethoxy]phenyl]methyl]-1,3-thiazolidine-2,4-dione, compound (4): (S)-5-[[4-[2-[5-(R)-(1-hydroxyethyl)pyridin-2-yl]ethoxy]phenyl]methyl]-1,3-thiazolidine-2,4-dione, and compound (5): (S)-5-[[4-[2-[5-(S)-(1-hydroxyethyl)pyridin-2-yl]ethoxy]phenyl]methyl]-1,3-thiazolidine-2,4-dione, or a pharmaceutically acceptable salt thereof, wherein the mixture is optically active.

4. The method according to claim 3, wherein the mixture comprises:
 (a) the compound (2) and the compound (3);
 (b) the compound (4) and the compound (5);
 (c) the compound (2) and the compound (4); or
 (d) the compound (3) and the compound (5),
 or a pharmaceutically acceptable salt thereof.

5. The method according to claim 1, wherein the dosage form comprises a mixture comprising each compound (2): (R)-5-[[4-[2-[5-(R)-(1-hydroxyethyl)pyridin-2-yl]ethoxy]phenyl]methyl]-1,3-thiazolidine-2,4-dione, compound (3): (R)-5-[[4-[2-[5-(S)-(1-hydroxyethyl)pyridin-2-yl]ethoxy]phenyl]methyl]-1,3-thiazolidine-2,4-dione, compound (4): (S)-5-[[4-[2-[5-(R)-(1-hydroxyethyl)pyridin-2-yl]ethoxy]phenyl]methyl]-1,3-thiazolidine-2,4-dione, and compound (5): (S)-5-[[4-[2-[5-(S)-(1-hydroxyethyl)pyridin-2-yl]ethoxy]phenyl]methyl]-1,3-thiazolidine-2,4-dione in an amount of 25%±5% w/w.

6. The method according to claim 1, further comprising administering another therapeutic agent.

7. The method according to claim 6, wherein the compound of formula (1), or a pharmaceutically acceptable salt thereof, and said another therapeutic agent are provided in combination.

8. The method according to claim 1, wherein no more than 1% of the total number of hydrogen atoms per mole of the compound of formula (1) are in the form of the $^2$H isotope.

9. The method according to claim 1, wherein the dosage form is an oral, intraoral, topical, epicutaneous, subcutaneous, transdermal, intramuscular, parenteral, ocular, rectal, vaginal, inhalation, buccal, sublingual, or intranasal dosage form.

10. The method according to claim 9, wherein the dosage form is an oral dosage form.

11. The method according to claim 10, wherein the oral dosage form is solid.

12. The method according to claim 11, wherein the oral solid dosage form is a tablet, a capsule, a pill, or a plurality of granules.

13. The method according to claim 10, wherein the oral dosage form is an oral solution or an oral suspension.

* * * * *

UNITED STATES PATENT AND TRADEMARK OFFICE
CERTIFICATE OF CORRECTION

| | |
|---|---|
| PATENT NO. | : 11,938,122 B2 |
| APPLICATION NO. | : 16/465043 |
| DATED | : March 26, 2024 |
| INVENTOR(S) | : Pizcueta Lalanza et al. |

It is certified that error appears in the above-identified patent and that said Letters Patent is hereby corrected as shown below:

In the Specification

In Column 10, Line 9, "20%" should read -- 20% ± --.

In Column 13, Line 43, "700" should read -- 70° --

In Column 16, Line 16, "PPAR-7" should read -- PPAR-$\gamma$ --.

In Column 16, Line 17, "PPAR-7" should read -- PPAR-$\gamma$ --.

In Column 18, Line 1, "interferon-3-la," should read -- interferon-$\beta$-1a, --.

In Column 19, Line 46, "CYP21B6," should read -- CYP2B6, --.

In Column 19, Line 48, "MIN4-102" should read -- MIN-102 --.

In Column 19, Line 50, "MIN4-102" should read -- MIN-102 --.

In Column 19, Line 54, "2B36," should read -- 2B6, --.

In Column 21, the subtitle on Line 41, "IN-102" should read -- MIN-102 --.

Signed and Sealed this
Eighth Day of October, 2024

Katherine Kelly Vidal
*Director of the United States Patent and Trademark Office*